(12) United States Patent
Yang et al.

(10) Patent No.: US 7,846,716 B2
(45) Date of Patent: Dec. 7, 2010

(54) MICROCHIP AND ANALYSIS METHOD USING THE SAME

(75) Inventors: Bo Yang, Asaka (JP); Yukio Sudo, Asaka (JP); Yoshiki Sakaino, Asaka (JP); Hideyuki Karaki, Minami-ashigara (JP); Akira Wakabayashi, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 921 days.

(21) Appl. No.: 11/413,138

(22) Filed: Apr. 28, 2006

(65) Prior Publication Data

US 2006/0263242 A1     Nov. 23, 2006

(30) Foreign Application Priority Data

Apr. 28, 2005  (JP)  ............................. 2005-131357
Sep. 30, 2005  (JP)  ............................. 2005-288452

(51) Int. Cl.
*C12M 1/36* (2006.01)

(52) U.S. Cl. ............... 435/286.5; 435/287.1; 435/288.5; 416/61

(58) Field of Classification Search ...................... 435/6, 435/287.2; 204/452; 222/134
See application file for complete search history.

(56) References Cited

U.S. PATENT DOCUMENTS

| | | | |
|---|---|---|---|
| 5,092,973 A | 3/1992 | Zare et al. | |
| 5,208,163 A | 5/1993 | Charlton et al. | |
| 5,219,762 A | 6/1993 | Katamine et al. | |
| 2002/0045272 A1* | 4/2002 | McDevitt et al. | 436/518 |
| 2002/0119482 A1* | 8/2002 | Nelson et al. | 435/6 |
| 2002/0150512 A1 | 10/2002 | Kellogg et al. | |
| 2002/0195463 A1 | 12/2002 | Seki et al. | |
| 2003/0077204 A1 | 4/2003 | Seki et al. | |
| 2003/0166302 A1 | 9/2003 | Shigenobu et al. | |
| 2004/0166504 A1* | 8/2004 | Rossier et al. | 435/6 |
| 2004/0209381 A1 | 10/2004 | Peters et al. | |

FOREIGN PATENT DOCUMENTS

| | | |
|---|---|---|
| EP | 0 376 611 A2 | 7/1990 |
| EP | 0376133 A | 7/1990 |
| EP | 1385002 A | 1/2004 |
| JP | 2-245655 A | 10/1990 |
| JP | 3-226666 A | 10/1991 |
| JP | 8-122335 A | 5/1996 |
| JP | 8-233778 A | 9/1996 |

(Continued)

OTHER PUBLICATIONS

Dry Chemistry, Modern Medical Laboratory (Kensa To Gijutsu), vol. 21, No. 5, Igaku Shoin, pp. 328-333, 1993.

*Primary Examiner*—N. Yang
(74) *Attorney, Agent, or Firm*—Birch, Stewart, Kolasch & Birch, LLP

(57) ABSTRACT

An object of the present invention is to provide a microchip whereby, when chemical analysis is conducted, a specimen liquid can be directly collected and weighed without using any collecting and weighing devices. The present invention provides a microchip for analyzing liquid samples, which has a measuring structure for weighing and collecting a given amount of a specimen liquid within a range of 0.05 to 10 μl from an excessive amount of the specimen liquid which was introduced in the chip, wherein the measuring structure is located at the upstream side of an analysis element for analyzing a target substance in the specimen liquid inside the microchip.

3 Claims, 17 Drawing Sheets

FOREIGN PATENT DOCUMENTS

| | | |
|---|---|---|
| JP | 10-142177 A | 5/1998 |
| JP | 2002-071684 | 3/2002 |
| JP | 2002-357616 A | 12/2002 |
| JP | 2004-157097 A | 6/2004 |
| JP | 2004-163104 A | 6/2004 |
| JP | 2004-354388 | 12/2004 |
| WO | WO 02/18953 A1 | 3/2002 |
| WO | WO-2004/062801 | 7/2004 |

* cited by examiner

Fig.1
Fig.1 (a)
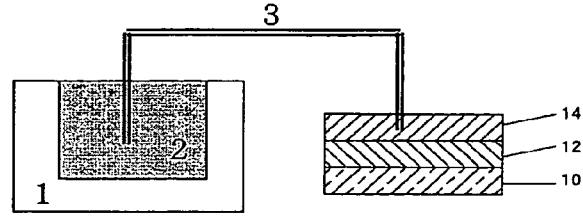
Fig.1 (b)
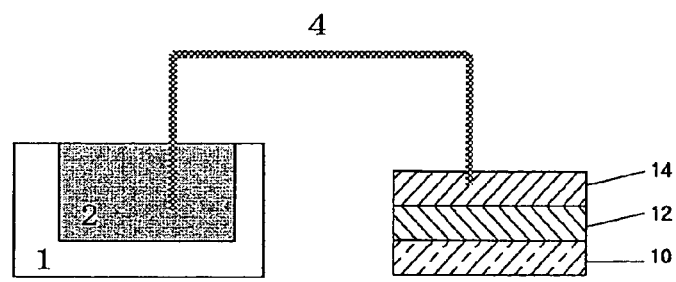
Fig.1 (c)
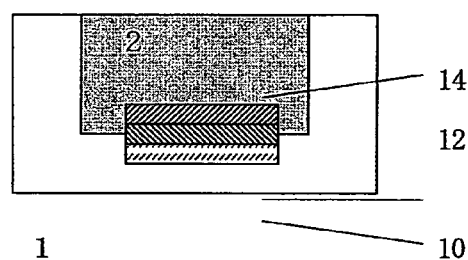
Fig.1 (d)
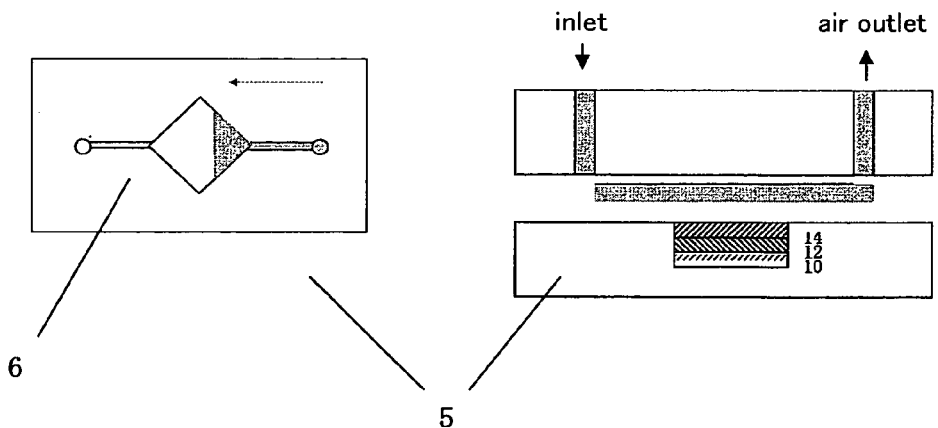

pattern I pattern II (a)

(b)

(c)

MICROCHIP AND ANALYSIS METHOD USING THE SAME

TECHNICAL FIELD

The present invention relates to a microchip used for analyzing test components contained in specimens such as: blood, body fluid, or urine of humans or other animals; fresh water; seawater; soil extracts; extracts of agricultural products, fishery products and processed food; and liquid samples used for natural scientific studies, and an analysis method. Specifically, the present invention relates to a measuring chip having a structure capable of weighing a trace amount of liquid which is used for the analysis or performance of chemical reactions that involves the use of various samples, and a testing method using the same.

BACKGROUND ART

Generally, in the case of conducting analysis based on a chemical reaction, it is necessary that liquids such as samples and reactive reagents be quantitatively weighed and collected so as to be subjected to quantitative reaction so that precise analysis results can be obtained. In particular, as conducting microanalysis such as blood analysis, it is necessary that a liquid such as specimen or a reactive reagent be weighed with high precision so that it can be supplied to a reaction site.

Hitherto, substances in a liquid specimen have been quantified by the following operation: a liquid such as a specimen or a reactive reagent is weighed using a collecting device (pipet, micropipet, syringe, etc.); a given amount of the liquid weighed is supplied to a reaction vessel; reaction is performed; and thus a target substances in the specimen are quantified based on reaction signals.

In general, a conventional wet chemistry analysis method is complicated, and the handling and procedures relating to apparatuses used for analysis are not simple. For instance, in the case of blood analysis, it is necessary to use a combination of many reagent solutions handled in different ways so as to measure a single blood component. When measuring glycohemoglobin (HbA1c) in blood using a blood analyzer (7170; Hitachi), 240 µl of a reagent solution 1 and 8.0 µl of HbA1c are separately collected and weighed, mixed, and allowed to react with each other at 37° C. for 5 minutes. Then, 80 µl of a reagent solution 2 is weighed, and is added thereto. After being kept at 37° C. for 5 minutes, the resultant is quantified by a 2 point-end method (dominant wavelength: 450 nm; complementary wavelength: 800 nm) (International Publication WO02/018953).

To measure glycohemoglobin (HbA1c) in blood as described above, a collecting and weighing device (1), a vessel for mixing a specimen and a reagent, and operation for supplying a specimen liquid, for example, are required, making the configuration and the operation for the measurement complicated. In addition, many forms of disposal waste (chips, mixing vessels, washes, etc.) are generated due to the measurement, and this has been problematic.

On the other hand, dry chemistry analysis method has been developed, wherein reagents and the like, which are necessary for detection of a specific component, are contained in a dry state ("11. Other analysis methods (*Sonota no Bunseki Ho*): (1) Dry Chemistry," Yuzo Iwata, "Manual for Clinical Chemistry Practice (*Rinsho Kagaku Jissen Manual*)," Igaku Shoin, 1993, "Modern Medical Laboratory (*Kensa To Gijutsu*), extra number," vol. 21, no. 5, pp. 328-333). In accordance with the dry chemistry analysis method, all reagents necessary for qualitative/quantitative analysis are incorporated into an analysis element such as reagent paper, a disposable electrode, or a disposable magnetic material. Basically, a disposable analysis element capable of measuring a single component from a single specimen is used. Thus, rapid blood analysis using a relatively small amount of blood (about 10 µl) can readily be conducted (JP Patent Publication (Kokai) No. 8-122335 A (1996)). A large number of analyzers using a dry chemistry analysis method have been developed and commercialized. Examples thereof that are commercially available include Fuji Drychem (Fujifilm), Ektachem (Eastman Kodak, U.S.), Drylabo (Konica), Spotchem (Kyoto Daiichi Kagaku), Reflotron (Boehringer Mannheim, Germany), and Seralyzer (Miles Laboratories; U.S.). Upon dry chemistry analysis, operation whereby a specimen liquid is supplied so that it can be mixed with a reagent is not required. However, a collecting and weighing device and a collecting operation are still required.

Further, in recent years, home care has been proposed as a response to a sharp increase in medical costs due to the rapid transition to an aging society and the development of advanced medical therapies. In addition, home care, which is supposed to be a core of the future medical system, has been discussed in terms of specific ways of implementing it. To correspond to such situation, in the home care system, it is preferable to use a blood analysis method whereby a plurality of components can be rapidly measured with good precision using a minute amount of blood and a small-sized apparatus in a convenient manner.

Thus, to solve the above problems, application of a µTAS (micro total analysis system) technology, whereby a conventionally used analyzer can be downsized and a trace amount of a liquid reagent is allowed to react, has been discussed. With µTAS technology, in order to collect a minute amount of a specimen such as blood or the like, a groove is formed on the surface of a chip made of glass, silicon, or resin, the size of which is several to ten square centimeters. Then, a reagent solution or a specimen is poured into the groove such that separation or reaction is carried out. Thus, analysis of a minute amount of a sample is conducted (JP Patent Publication (Kokai) No. 2-245655 A (1990), JP Patent Publication (Kokai) No. 3-226666 A (1991), JP Patent Publication (Kokai) No. 8-233778 A (1996), JP Patent Publication (Kokai) No. 10-142177 A (1998), and Analytical Chem. 69, 2626-2630 (1997) Aclara Biosciences). When using this technique, a minute amount of a sample and a reagent that is necessary for detection must be collected and weighed in a chip. However, since the amount of a specimen liquid handled is extremely small, it is difficult to quantitatively collect and weigh such liquid. Thus, a complicated configuration is required to collect and weigh such liquid, resulting in a complicated operation for handling the configuration, which has been problematic.

In JP Patent Publication (Kokai) No. 2004-163104 A, a structure for collecting and weighing a small amount of a liquid is provided for a channel of a microchip so that capillarity (capillary repulsion) generated by the liquid in the channel is utilized. In accordance with JP Patent Publication (Kokai) No. 2004-163104 A, a structure for collecting and weighing a small amount of a liquid is provided for various types of apparatuses in which it is necessary to handle a liquid in a conventional quantitative manner such that reduction of the dead volume of a sample, downsizing of the apparatus used in its entirety, and costsaving can be achieved. However, in the case of the technique disclosed in JP Patent Publication (Kokai) No. 2004-163104 A, it is necessary to design a channel in a microchip, impart hydrophilicity or hydrophobicity to the channel, and feed a liquid into the channel by air pressure.

Thus, it is difficult to say that such method is a convenient method for weighing a small amount of liquid quantitatively.

Further, as techniques for collecting and weighing a trace amount of liquid include those disclosed in JP Patent Publication (Kokai) No. 2002-357616 A and JP Patent Publication (Kokai) No. 2004-157097 A, for example. When these techniques are employed, a trace amount of liquid can be quantitatively handled with a microchip provided with a plurality of fluid channels in which liquid continuously flows. However, a liquid transport system is needed for liquid operation and various construction in microchip.

SUMMARY OF THE INVENTION

A first object of the present invention is to provide a microchip whereby, when chemical analysis is conducted, a specimen liquid can be directly collected and weighed without using any collecting and weighing devices so that the specimen liquid can be supplied to a reaction part, and a method for weighing a liquid and a quantitative method can readily be carried out with high precision. Further, a second object of the present invention is to provide a microchip in which microweighing can be achieved, although it has been difficult to precisely perform microweighing in a microchip by a conventional weighing method.

As a result of intensive studies to solve the above problems, the present inventors have found that the above objects can be achieved by bonding a porous material to an analysis element using saturated water absorption of the porous material.

That is, the present invention provides the followings.

(1) A microchip for analyzing liquid samples, which has a measuring structure for weighing a given amount of a specimen liquid within a range of 0.05 to 10 µl from an excessive amount of the specimen liquid which was introduced in the chip, wherein the measuring structure is located at the upstream side of an analysis element for analyzing a target substance in the specimen liquid inside the microchip.

(2) The microchip of (1) wherein the measuring structures and the analysis elements are provided at a plurality of parts inside the microchip.

(3) The microchip of (1) wherein the measuring structures is a porous material membrane capable of containing a given amount of a specimen liquid, and the microchip has a structure such that a specimen liquid contained in the porous material membrane is introduced into the analysis element.

(4) The microchip of (3) wherein the porous material membrane comprises an organic porous material.

(5) The microchip of (3) wherein the porous material membrane comprises an inorganic porous material.

(6) The microchip of (3) wherein the porous material membrane comprises one or more types of porous material.

(7) The microchip of (1) wherein the measuring structure is a structure of fluid channel, and has a first fluid channel provided on the chip body, a second fluid channel in communication with the first fluid channel at one of its ends; and a third fluid channel in communication with the other end of the second fluid channel, wherein, when the perimeter and the cross-sectional area of the vicinity of an opening of the first fluid channel in communication with the second fluid channel are designated as L1 and S1, respectively, and the perimeter and the cross-sectional area of the first opening of the second fluid channel in communication with the first fluid channel are designated as L2 and S2, respectively, the formula (L1/S1)<(L2/S2) is satisfied, and wherein the first opening of the second fluid channel is provided with a level difference in at least a part thereof, and the second opening of the second fluid channel in communication with the third fluid channel is provided with a level difference in at least a part thereof.

(8) The microchip of (7) wherein the perimeter of the first opening provided with a level difference is at least a half of the perimeter L2 of the first opening of the second fluid channel.

(9) The microchip of (7) wherein the perimeter of the second opening provided with a level difference is at least a half of the perimeter of the second opening.

(10) The microchip of (1) wherein the analysis element is a dry analysis element or an electrode.

(11) A method for analyzing a target substance wherein a target substance in a specimen liquid is analyzed by using the microchip of (1).

(12) The method of (11) which comprises introducing a specimen liquid into the microchip of (1), introducing the specimen liquid from the measuring structure to the analysis element, and detecting a target substance in the analysis element.

(13) The method of (11) wherein the specimen liquid is blood or urine.

(14) The method of (11) wherein the specimen liquid food.

(15) The method of (11) wherein the specimen liquid is an environment-related substance.

BRIEF DESCRIPTION OF THE DRAWINGS

FIG. 1 is a diagram showing a method for supplying a liquid to a porous material layer used for weighing. In the figure, numerical reference 1 denote a liquid tank, 2 denotes a specimen liquid, 3 denotes a capillary, 4 denotes a porous bridge, 5 denotes a PDMS cell, 6 denotes a channel, 14 denotes a porous material layer (weighing layer and development layer), 12 denotes a reagent layer (reaction layer), and 10 denotes a transparent substrate.

BEST MODE FOR CARRYING OUT THE INVENTION

Figure 2:
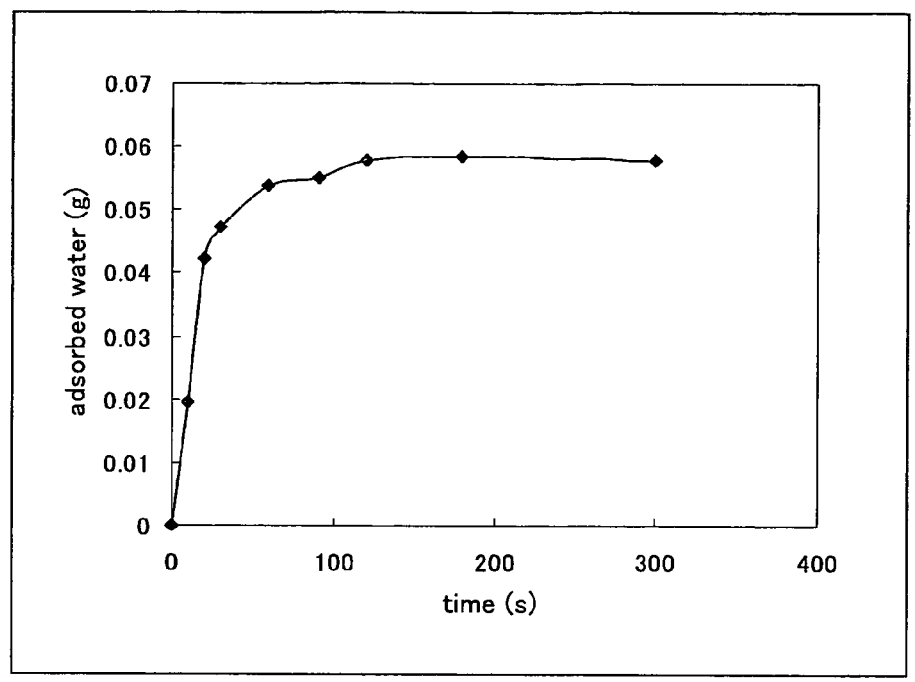
FIG. 2 shows a time course change of weight by water absorption when the porous material layer used for weighing is a textile.

Embodiments of the present invention will be described below.

The microchip used for liquid sample analysis of the present invention is characterized in that it has a measuring structure for weighing a given amount of a specimen liquid within a range of 0.05 to 10 μl from an excessive amount of the specimen liquid which was introduced in the chip, and the measuring structure is located at the upstream side of an analysis element for analyzing a target substance in the specimen liquid inside the microchip. With the use of the microchip of the present invention, by bonding an organic or inorganic porous material to an analysis element, it is possible that weighing the liquid, supplying it to an analysis part, and detecting it by reaction are performed in one step.

An example of the microchip of the present invention is a microchip in which an inlet and an outlet for a specimen such as blood and a channel connecting between the inlet and the outlet are provided, and an analysis element used for detection of a test component in the specimen is provided in the middle of the channel. To precisely measure a test component in a specimen using such microchip, it is necessary to precisely collect a given amount of a specimen supplied to a microchip so as to supply it to an analysis element. In accordance with the present invention, with the use of a porous material membrane that absorbs a given amount of a specimen liquid when coming into contact with an excessive amount of the specimen liquid, it has become possible to collect a given amount of the specimen in a minute amount. In addition, by adopting a structure such that a specimen liquid in a channel or a liquid tank is introduced into an analysis element by passing through a porous material membrane, it has become possible to directly analyze a given amount of the specimen collected.

The porous material used in the present invention may be a fiber material or a non-fiber material, as long as it has the property of being able to absorb a given amount of a specimen liquid when coming into contact with excessive amount of the specimen liquid. Examples of such fiber material that can be used include filter paper, nonwoven cloth, woven cloth (e.g., woven cloth disclosed in JP Patent Publication (Kokai) No. 55-164356 A (1980) or JP Patent Publication (Kokai) No. 57-66359 A (1982)), textiles (e.g., a textile disclosed in JP Patent Publication (Kokai) No. 60-222769 A (1984)), and glass fiber filter paper.

Examples of such non-fiber material that can be used include a non-fiber isotropic porous material layer such as a porous material layer continuously containing fine pores in which a membrane filter (brush polymer layer), polymer microbeads, glass microbeads, and diatomaceous earth are retained by a hydrophilic polymer binder (disclosed in JP Patent Publication (Kokoku) No. 53-21677 B (1978), U.S. Pat. No. 3,992,158, and the like); and a non-fiber isotropic porous material layer comprising a porous material layer continuously containing fine pores (three-dimensional lattice granular structure layer) in which polymer microbeads are bonded to one another in a point contact state using a polymer adhesive agent that does not become swollen with water (disclosed in JP Patent Publication (Kokai) No. 55-90859 A (1980)).

As a porous material membrane, a porous membrane comprising an organic polymer may also be used. Specifically, such porous membrane that can be used is made of 6,6-nylon, 6-nylon, acrylate copolymer, polyacrylate, polyacrylonitrile, polyacrylonitrile copolymer, polyamide, polyimide, polyamideimide, polyurethane, polyethersulfone, polysulfone, mixture of polyethersulfone and polysulfone, polyester, polyester carbonate, polyethylene, polyethylene-chlorotrifluoroethylene copolymer, polyethylene-tetrafluoroethylene copolymer, polyvinyl chloride, polyolefin, polycarbonate, polytetrafluoroethylene, polyvinylidenedifluoride, polyphenylene sulphelene sulfide, polyfluorocarbonate, polyporopylene, polybenzimidazole, polymethylmethacrylate, styrene-acrylonitrile copolymer, styrene-butadiene copolymer, saponified product of ethylene-vinyl acetate copolymer, polyvinyl alcohol, saponifed product of cellulose acetate butyrate, cellulose acetate butyrate butyrate, or a mixture thereof.

Preferably, a laminate disclosed in one of the following patent documents is used, each of which comprises a plurality of porous membranes that have been partially bonded to each other: JP Patent Publication (Kokai) No. 61-4959 A (1986) (corresponding to U.S. Pat. No. 5,019,347, and EP 0166365A); JP Patent Publication (Kokai) No. 62-116258 A (1987); JP Patent Publication (Kokai) No. 62-138756 A (1987) (corresponding to EP 0226465A); JP Patent Publication (Kokai) No. 62-138757 A (1987) (corresponding to EP 0226465A); JP Patent Publication (Kokai) No. 62-138758 A (1990) (corresponding to EP 0226465A); and the like.

In addition, preferably, the following substances may be used: polymer gels (naturally occurring polymer gels: gelatin, agar, agaropectin, starch, amylose, amylopectin, carrageenan, gellan gum, xanthan gum, curdlan, collagen, alginic acid, pectin, konjakmannan, methylcellulose, hydroxypropyl cellulose, and dextran; and synthetic polymer gels: polyethylene, polystyrene, polyacrylate, polyacrylic acid, polymethacrylic acid, polyglutamic acid, polyvinylpyridine, polyvinylimidazole, acrylamide, vinylpyrrolidone, hydroxyethyl methacrylate, O-benzil-L-glutamate, polyethylene glycol, and hyaluronic acid); latex particles; and inorganic materials (porous carbon, porous silicon carbide, porous glass beads, silicagel, alumina oxide, zeolite, and mesoporous materials).

Inside the microchip of the present invention, an analysis element used for analysis of a target substance in a specimen liquid is provided. The microchip has a structure such that a specimen liquid in a channel or a liquid tank passes through a porous material membrane so as to be introduced into the analysis element.

The analysis element used in the present invention may be a dry analysis element based on colorimetry or an electrode. However, particularly preferably, the element is a dry analysis element.

The dry analysis element that can be used in the present invention is one in which all or some reagents necessary for qualitative/quantitative analysis of components in blood that are subjected to measurement are incorporated into at least one layer of such element. It means that it is an analysis element that makes use of so-called dry chemistry. Specific examples of such multilayer dry analysis element include those described in "Fujifilm Research & Development," vol. 40, p. 83 (published in 1995, Fujifilm) and "Current Review of Clinical Pathology (*Rinsho Byori*)," extra edition, special issue: no. 106, "Dry Chemistry: New development in rapid tests (*Kanni Kensa no Aratanaru Tenkai*)" (published in 1997, Clinical Pathology Press (*Rinsho Byori Kankokai*)).

In general, the aforementioned multilayer dry analysis element comprises at least one functional layer. As long as the element comprises at least one functional layer, the element may comprise one functional layer or two or more functional layers, but it is not particularly limited thereto.

Specific examples of such functional layer include an adhesive layer that bonds a development layer with such functional layer, an absorptive layer that absorbs a liquid reagent, a mordant layer that prevents diffusion of a dye generated by a chemical reaction, a gas transmissive layer that selectively transmits a gas, an intermediate layer that suppresses or promotes mass transfer between layers, a light-shielding layer that is provided such that reflective photometry is stably conducted, a color-shielding layer that suppresses influence due to endogeneous pigments; a reagent layer that contains a reagent which reacts with a substance to be analyzed, and a color development layer that contains a coloring agent.

In an example of such multilayer dry analysis element, a hydrophilic polymer layer as a functional layer may be provided on a substrate, if necessary, via another layer such as an undercoated layer. Examples of such hydrophilic polymer layer that can be provided include a nonporous, water-absorbing, and water-permeable layer. A water-absorbing layer that basically consists of a hydrophilic polymer, a reagent layer that contains a hydrophilic polymer as a binder and a part or all of a coloring reagent which is directly involved in color reaction, and a detection layer that contains a component (e.g., mordant dye) which fixes and stabilizes a coloring dye in a hydrophilic polymer, and the like are provided.

(Reagent Layer)

A reagent layer is a water-absorbing and water-permeable layer, in which at least some parts of a reagent composition, which reacts with a test component in an aqueous liquid so as to generate an optically detectable change, are substantially uniformly dispersed in a hydrophilic polymer binder. Such reagent layer contains an indicator layer, a coloring layer, and other layers.

A hydrophilic polymer that can be used as a binder of a reagent layer is a naturally occurring or synthetic hydrophilic polymer. The swelling rate of such polymer upon water absorption is usually from about 150% to about 2000%, and preferably from about 250% to about 1500%, at 30° C. Examples of such hydrophilic polymer include gelatin (e.g., acid-treated gelatin and deionized gelatin), gelatin derivatives (e.g., phthalized gelatin and hydroxyacrylate graft gelatin), agarose, pullulan, pullulan derivatives, polyacrylamide, polyvinyl alcohol, polyvinylpyrrolidone and the like disclosed in, for example, JP Patent Publication (Kokai) No. 60-108753 A (1985).

Using a cross-linking agent, it is possible to render a reagent layer as a cured layer by cross-linking, if necessary. Examples of the cross-linking agent include a known vinyl-sulfone cross-linking agent such as 1,2-bis(vinylsulfonylacetamide)ethane, bis(vinylsulfonylmethyl)ether used for curing gelatin, aldehyde for curing a methallyl alcohol copolymer, and epoxy compounds containing two glycidyl groups.

The thickness of a reagent layer after being dried is preferably from about 1 μm to about 100 μm, and more preferably from about 3 μm to about 30 μm. In addition, preferably, a reagent layer is substantially transparent.

As a reagent contained in the reagent layer and other layers of a multilayer dry analysis element, the suitable reagent for detection of a corresponding test substance can be selected.

(Light-Shielding Layer)

A light-shielding layer may be provided on the aforementioned reagent layer according to need. A light-shielding layer is a water-transmissive or water-permeable layer, in which fine particles having light absorptivity or light reflectivity (both terms indicate light-shielding ability) are dispersed and retained in a small amount of hydrophilic polymer binder that has the ability to form a coating. When conducting reflective photometry from the side of a substrate that has light transmissivity so as to detect detectable changes (color change, color development, etc.) generated in a reagent layer, the light-shielding layer shields the color of an aqueous liquid that has impregnated and has been supplied to a development layer described below; particularly, the red color of hemoglobin when the specimen is whole blood. Also, the light-shielding layer functions as a light-reflecting layer or a background layer.

Examples of the fine particles that have light reflectivity include titanium dioxide fine particles (e.g., fine crystal particles having a particle size of about 0.1 μm to about 1.2 μm of rutile, anatase, or brookite titanium dioxide), barium sulfate fine particles, and aluminium fine particles or fine flakes. Examples of light-absorptive fine particles include carbon black, gas black, and carbon microbeads. Of these, titanium dioxide fine particles and barium sulfate fine particles are preferable. Particularly preferably, anatase titanium dioxide fine particles are used.

There are examples of a hydrophilic polymer binder that except for a hydrophilic polymer such as the aforementioned hydrophilic polymer used for producing a reagent layer could form a coating the weak hydrophilic regenerated cellulose and cellulose acetate. Inside of these polymers, gelatin, gelatin derivatives and polyacrylamide are used preferably. In addition, gelatin and gelatin derivatives can be used by mixing a known curing agent (cross-linking agent) therewith.

A light-shielding layer can be provided in a manner such that an aqueous dispersion containing light-shielding fine particles and a hydrophilic polymer is applied onto a reagent layer and is dried by a known method. In addition, instead of a light-shielding layer, light-shielding fine particles may be contained in the aforementioned development layer.

(Detection Layer)

In general, a detection layer is a layer in which a dye generated in the presence of a test component, diffuses so as to be optically detected through a light-transmissive substrate. The detection layer can be composed of a hydrophilic polymer. The detection layer may contain a cationic polymer for detection of a mordant dye such as an anionic dye. In general, a water-adsorbed layer indicates a layer in which a dye generated in the presence of a test component does not substantially diffuse. At this point, a water-adsorbed layer is distinguished from a detection layer.

A multilayer dry analysis element can be prepared by a known method. The element can be used by cutting it to about 5 mm- to 30 mm-square chips or round chips, the sizes of which are almost the same as those of the square chips.

Many of such multilayer dry analysis elements have been developed and commercialized. One example thereof is Fuji Drichem (Fujifilm). In the present invention, such multilayer dry analysis element is used, or a part thereof can be used.

A method for bonding a porous material layer to an analysis element is not particularly limited. However, it is preferable to bond such porous material layer to a multilayer dry analysis element via an adhesive layer. A porous membrane can adhere to a multilayer dry film by being tightly bound to a multilayer dry film when an adhesive layer is moistened with water or swollen due to water adsorption at room temperature while applying pressure of 3 to 5 kg/cm$^2$. Thus, preferably, an adhesive layer comprises a hydrophilic polymer such that the individual layers are bound together. Preferred examples of hydrophilic polymers that can be used for producing such adhesive layer include gelatin, gelatin derivatives, and polyacrylamide. The thickness of the adhesive layer after being dried is generally between about 0.5 μm to about 20 μm, and preferably between about 1 μm and about 10 μm.

A porous material membrane (measuring layer) as an independent measuring (weighing) layer may come into contact with an analysis element part. Also, a porous material membrane as a measuring layer may be mixed with an analysis element part. For instance, when an analysis element is a multilayer dry analysis element, a porous material measuring layer may function as a development layer and a reagent layer at the same time. When an analysis element is an electrode, it is convenient to directly use an electrode made of porous material (e.g., carbon black).

For the purposes of improving the precision of liquid weighing and the liquid supply rate using a porous material, wettability of a porous material with respect to the liquid to be weighed is important. Since the quantity of liquid to be weighed in a uniform porous material with good wettability is proportional to the surface area of the material, such porous material has a measuring function. Simultaneously, capillarity of a porous material layer largely increases the development rate of liquid. Thus, preferably, a porous material layer is treated so as to obtain hydrophilicity or hydrophobicity. Hydrophilic treatment is necessary in case of an aqueous specimen, and hydrophobic treatement is necessary in case of an oil specimen. To impart hydrophilicity or hydrophobicity, conventional surface treatment methods can be applied. Such methods can be roughly divided into chemical surface treatment methods and physical surface treatment methods. The chemical surface treatment methods include chemical treatment, coupling agent treatment, vapor treatment, grafting, electrochemical methods, and surface modification using additives. The physical surface treatment methods include UV irradiation, electron beam treatment, ion beam irradiation, low-temperature plasma treatment, casing treatment, glow discharge treatment, corona discharge treatment, and oxygen plasma treatment.

When liquid is weighed by using a porous material, the quantity of the liquid to be weighed can be controlled by controlling the saturated water absorption of the porous material. Factors that influence the saturated water absorption of the porous material are (1): the size of the porous material layer (membrane); and (2): the type of the porous material. The quantity of the liquid to be weighed in a uniform porous material with good wettability is proportional to the surface area of the material. By utilizing such properties, the quantity of the liquid to be weighed can be controlled by changing the size of the porous material layer (membrane). In addition, the saturated water absorption differs in accordance with the type of the porous material (e.g., the saturated water absorption of cloth is twice of that of a PS membrane (polysulfone membrane, Fujifilm)). By utilizing such properties, the quantity of the liquid to be weighed also can be controlled.

As a method for supplying liquid to a porous material layer, the liquid is fed by using a capillary (FIG. 1(a)) or a porous material (cloth, paper, hollow fiber, etc.) (FIG. 1(b)), by immersing the porous material used for weighing in a liquid (FIG. 1(c)), or by using a channel (FIG. 1(d)).

Hereafter, the preferred embodiments of the present invention are described in detail with reference to the drawings.

Figure 8:
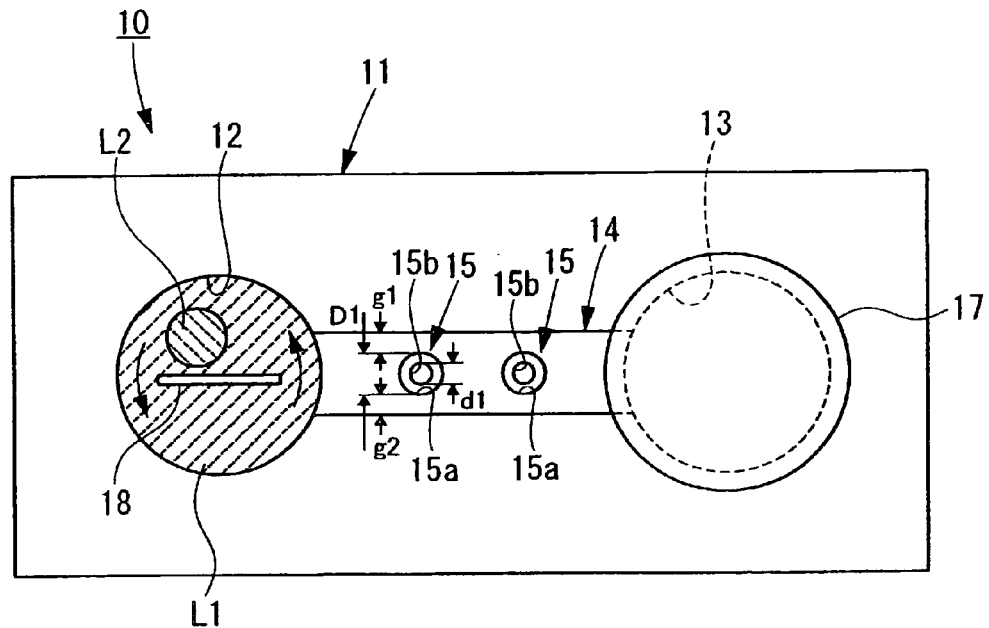
FIG. 8 shows the first embodiment of the measuring chip of the present invention
Figure 9:
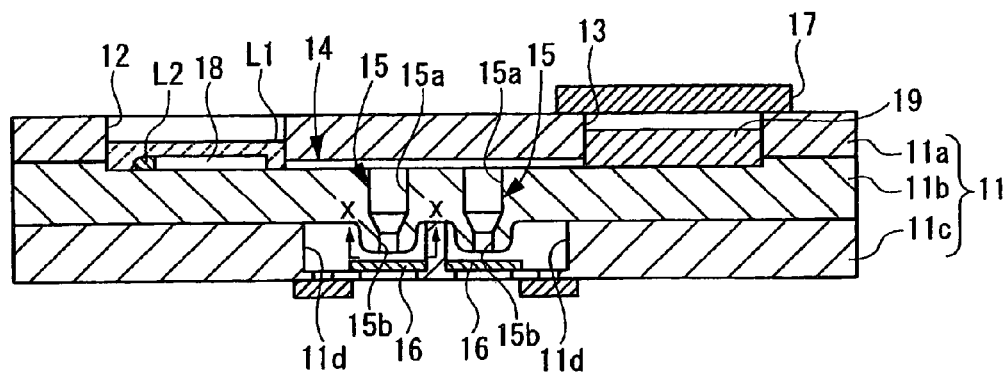
FIG. 9 is a cross sectional view of the first embodiment.
Figure 10:
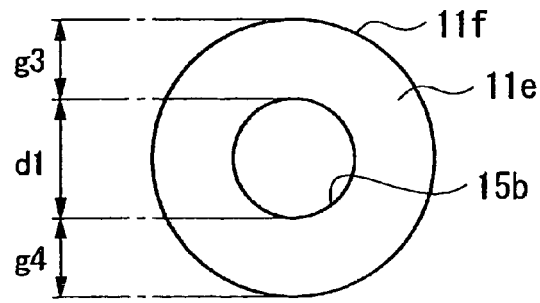
FIG. 10 is a cross sectional view as taken along section X-X of FIG. 9.
Figure 11:
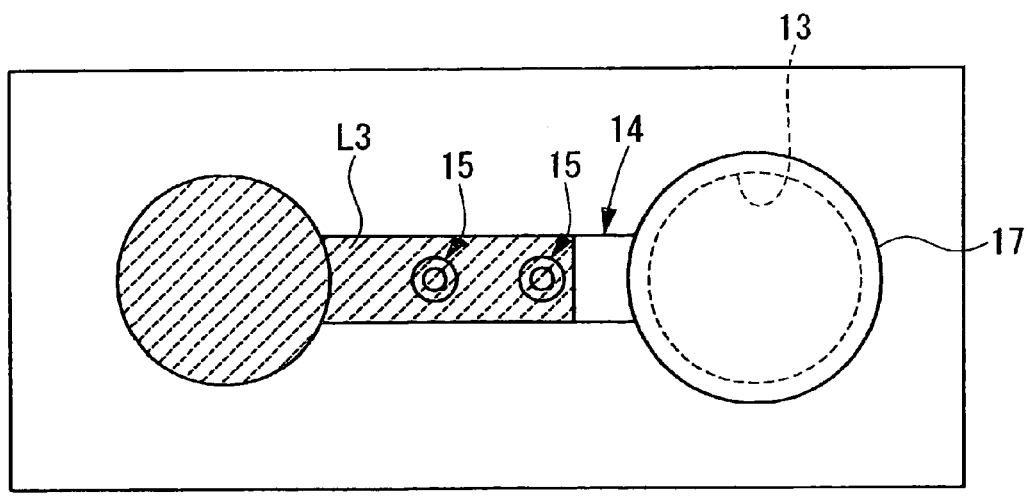
FIG. 11 illustrates the operations of the measuring chip according to the first embodiment.
Figure 12:
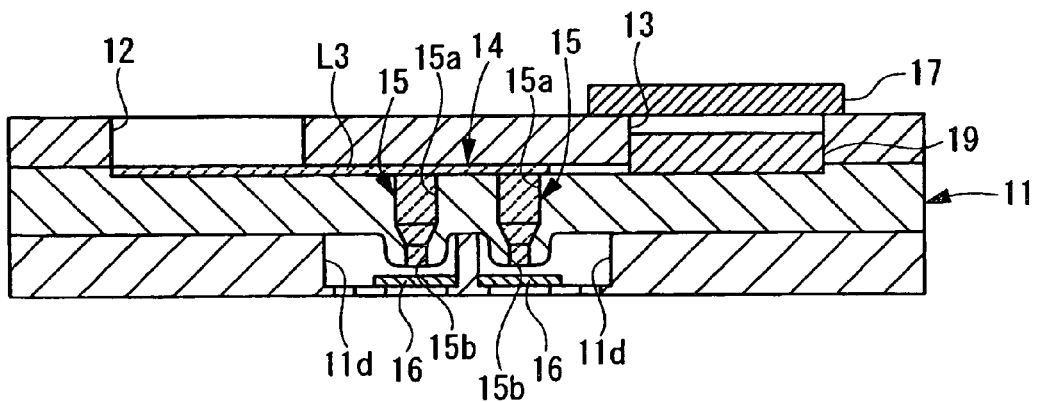
FIG. 12 is a cross sectional view of the measuring chip shown in FIG. 11.
Figure 13:
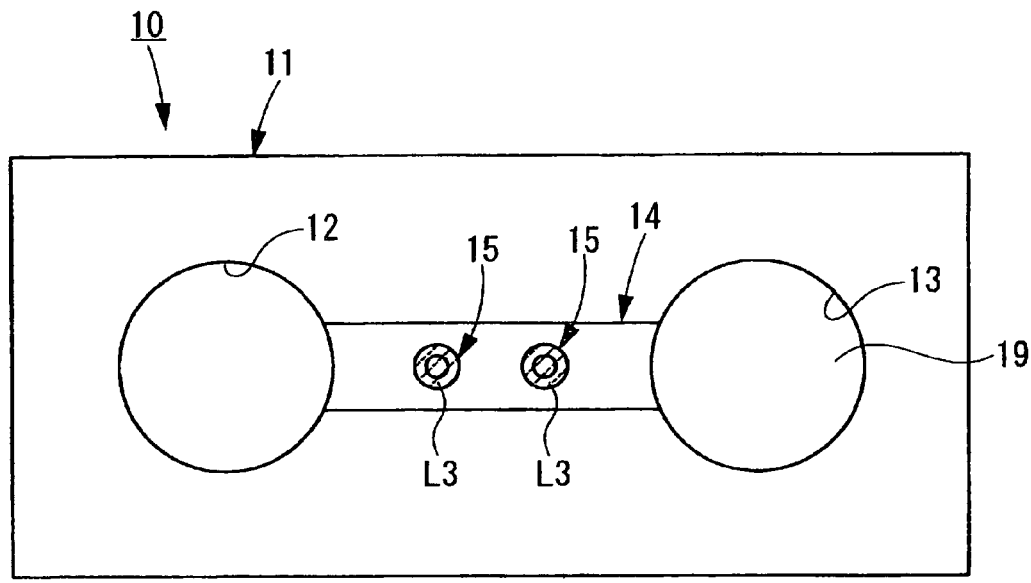
FIG. 13 illustrates the operations of the measuring chip according to the first embodiment.
Figure 14:
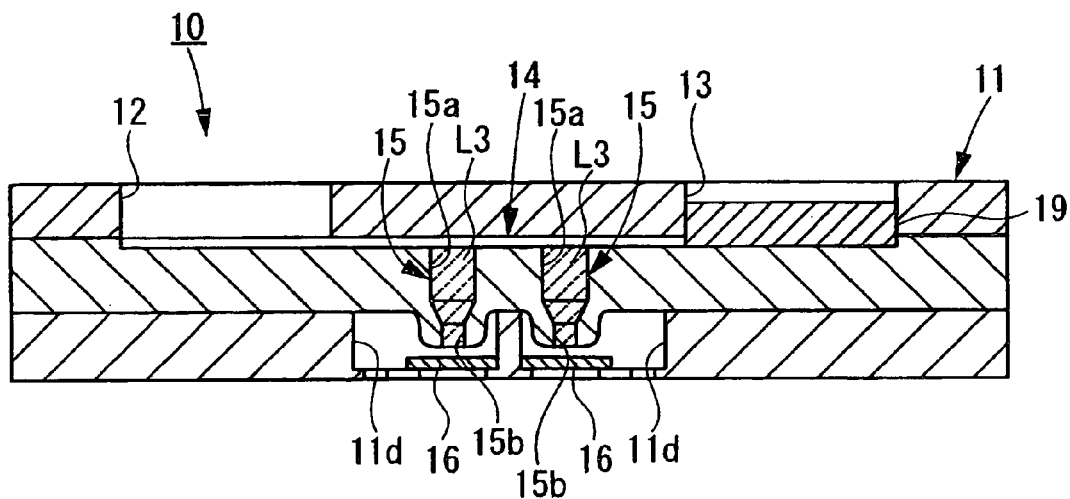
FIG. 14 is a cross sectional view of the measuring chip shown in FIG. 13.
Figure 15:
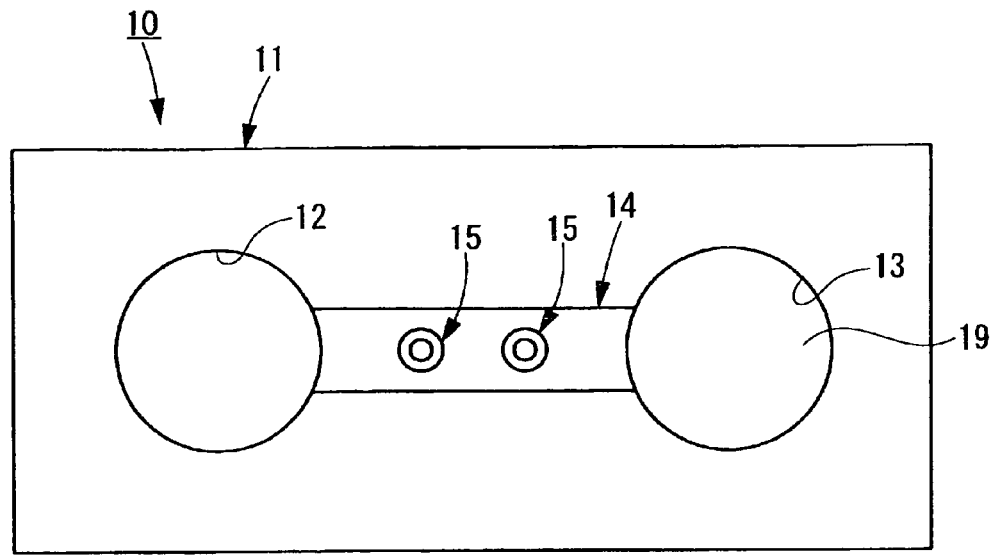
FIG. 15 shows the operations of the measuring chip according to the first embodiment.
Figure 16:
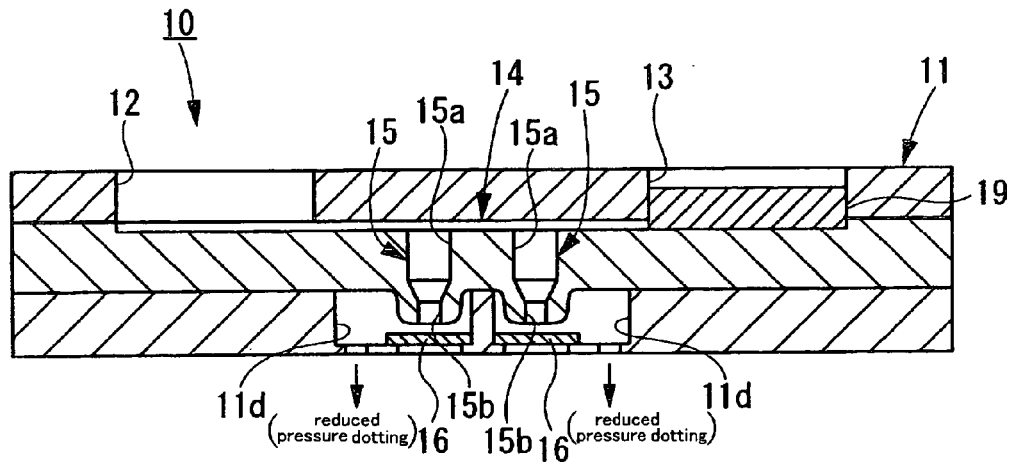
FIG. 16 is a cross sectional view of the measuring chip shown in FIG. 15.

FIG. 8 shows the first embodiment of the measuring chip of the present invention. FIG. 9 is a cross sectional view of the first embodiment. FIG. 10 is a cross sectional view as taken along section X-X of FIG. 9. FIG. 11 shows the operations of the measuring chip according to the first embodiment. FIG. 12 is a cross sectional view of the measuring chip shown in FIG. 11. FIG. 13 shows the operations of the measuring chip according to the first embodiment. FIG. 14 is a cross sectional view of the measuring chip shown in FIG. 13. FIG. 15 shows the operations of the measuring chip according to the first embodiment. FIG. 16 is a cross sectional view of the measuring chip shown in FIG. 15.

A measuring chip 10 of the present embodiment comprises a chip body 11. The chip body 11 is composed of a laminate of 3 chip substrates 11a, 11b, and 11c.

A diluent L1 and blood L2 are introduced into the chip body 11, and the chip body is provided with an agitation port 12 for agitating such two liquids and an absorption port 13 for absorbing residual liquid.

The agitation port 12 comprises, at its bottom, a rotatable bar-like agitation member 18 for agitating the diluent L1 and the blood L2 that have been introduced. As shown in FIG. 8, the diluent L1 and the blood L2 are agitated, and generated a test liquid L3 is then generated.

The absorption port 13 comprises a residual liquid-absorbing member 19 for absorbing the residual liquid with the effect of capillarity.

The first fluid channel 14 is provided between the agitation port 12 and the absorption port 13. In the present embodiment, the first fluid channel 14 is provided on the chip substrate 11b of the chip body 11.

The chip substrates 11b comprises thereon a plurality of second fluid channels 15 (2 channels in this embodiment) in communication with the first fluid channel 14. The second fluid channel 15 is in communication with the first fluid channel 14 at one of its ends and in communication with the third fluid channel 11d provided on the chip substrate 11c at the other end. The second fluid channel 15 has approximately cylindrical openings, and the diameter of the first opening 15a provided on the first fluid channel 14 side is larger than that of the second opening 15b provided on the third fluid channel 11d side. In this embodiment, the second fluid channel 15 functions as a measuring capillary that measures a given quantity of test liquid. The number of the second fluid channels 15 and that of the third fluid channels 11d corresponding to the second fluid channels 15 can be adequately altered in accordance with the number of times of testing or a type of testing.

The third fluid channel 11d comprises therein a reaction member 16 at the position diagonal to the second opening 15b of the second fluid channel 15. The reaction member 16 can be a slide for coloring reaction, for example.

A chip substrate may be made of an inorganic or organic material. Examples of inorganic materials that can be used for the substrate include metal, silicon, Teflon™, glass, and ceramic materials. Examples of organic materials include plastic and rubber materials.

Examples of plastic materials include COP, PS, PC, PMMA, PE, PET, and PP. Examples of rubber materials include natural rubbers, synthetic rubbers, silicone rubbers, and PDMS. Examples of silicon-containing materials include glass, quartz, amorphous silicons such as silicon wafer, and silicones such as polymethylsiloxane. Examples of particularly preferable materials include PMMA, COP, PS, PC, PET, PDMS, glass, and silicon wafer.

The inner surface of the chip is preferably hydrophilized or hydrophobized. Hydrophilizing treatment is necessary for an aqueous specimen, and hydrophobizing treatment is necessary for an oil specimen. Hydrophobization or hydrophilization can be carried out by using conventional surface treatment techniques. Such techniques are roughly classified into chemical surface treatment and physical surface treatment techniques. Examples of chemical surface treatment techniques include chemical treatment, surface treatment with a coupling agent, vapor treatment, grafting, electrochemical treatment, and surface modification with the use of an additive. Examples of physical surface treatment techniques include UV irradiation, electron beam treatment, ion beam irradiation, low-temperature plasma treatment, casing treatment, glow discharge treatment, corona discharge treatment, and oxygen plasma treatment.

A measurement range of a measuring chip can be optionally adjusted by changing the dimension of the measuring capillary (i.e., the second fluid channel 15). A measurement range is preferably between 0.05 μl and 50 μl, more preferably between 0.1 μl and 10 μl, and further preferably between 0.5 μl and 5 μl.

Subsequently, operations of the measuring chip of the present embodiment are described.

First, a diluent L1 and blood L2 are introduced into an agitation port 12, and these liquids are agitated with the use of an agitation member 18 to generate a test liquid L3, as shown in FIG. 8.

As shown in FIG. 11 and FIG. 12, when an outlet of the third fluid channel 11d is opened, the test liquid L3 reservoired in the agitation port 12 begins to flow toward the absorption port 13 by capillary force. At this time, the absorption port 13 is shielded by a shield member 17. A given amount of the test liquid L3 that flows through the first fluid channel 14 is reservoired and held in the second fluid channel 15.

Upon removal of the shield member 17 from the absorption port 13, the test liquid L3 reservoired in the first fluid channel 14 is guided into the absorption port 13 by capillary force, and the test liquid is absorbed by the residual liquid-absorbing member 19 by capillary force, as shown in FIG. 13 and FIG. 14. At this time, a given amount of the test liquid L3 is held in the second fluid channel 15. Also, a depressurization means (not shown) may be connected to the absorption port 13 to depressurize the inside of the first fluid channel 14.

As shown in FIG. 15 and FIG. 16, the test liquid L3 that has been held in the second liquid channel 15 is spot-deposited on the reaction member 16 via depressurization of the outlets of the third fluid channel 11d. Color is developed on the reaction member 16 to which the test liquid L3 has been spot-deposited, and the reaction member 16 is subjected to the determination of the absorbance.

In this embodiment, the test liquid L3 is spot-deposited on the reaction member 16 via depressurization; however, it may be carried out via pressurization from the upstream.

In the measuring chip 10 according to the present embodiment, when the perimeter and the cross-sectional area of the vicinity of an opening of the first fluid channel 14 in communication with the second fluid channel 15 are designated as L1 and S1, respectively, and the perimeter and the cross-sectional area of the first opening 15a of the second fluid channel 15 are designated as L2 and S2, respectively, then the formula (L1/S1)<(L2/S2) is satisfied. The above formula generally represents a pressure resistance with which a given amount of fluid can be retained in the vessel (referred to as the "Laplace pressure") while preventing such liquid from exuding from the opening provided at the bottom of the vessel. In the present invention, both liquids are the same test liquids L3 and thus, the surface tensions of the liquids are identical to each other. Specifically, when the liquid surface tension is designated as γ, the correlation (L1×γ/S1)<(L2×γ/S2) is attained. Since γ of one liquid is identical to that of the other liquid and γ is thus omitted from the formula, the correlation is represented by the formula (L1/S1)<(L2/S2). In the first embodiment, liquid drips in the vicinity of the opening when removing the liquid L3 remaining in the fluid channel 14, unless the above requirement is fulfilled. This results in incomplete removal of L3.

As shown in FIG. 8, the measuring chip 10 of the present embodiment comprises the first opening 15a provided with a level difference in at least a part thereof. More specifically, the periphery portion of the first opening 15a is located at the position of a gap g1 or g2 away from the inner surface of the first fluid channel 14, as shown in the top view of the measuring chip 10 (the front elevational view of FIG. 8). Thus, the boundary between the first opening 15a and the bottom of the first fluid channel 14 on the periphery portion of the first opening 15a becomes a level difference. It is preferable that the perimeter of the first opening 15a provided with a level difference be at least a half of the total perimeter L2 of the first opening 15a. In this example, both perimeters are 1.

As shown in FIG. 9 and FIG. 10, the second opening 15b of the second fluid channel 15 is formed at a cylinder-shaped protrusion 11e protruding into the third fluid channel 11d from the chip substrate 11b. The second opening 15b is located at the position of a gap g3 (=g4) away from the periphery portion 11f of the protrusion 11e. The boundary between the second opening 15b and the protrusion 11e becomes a level difference. It is preferable that the perimeter of the second opening 15b provided with a level difference be at least a half of the total perimeter of the second opening. In this example, both perimeters are 1.

In this embodiment, the diameter D1 of the first opening 15a was set between 0.5 mm and 1.5 mm, and the diameter d1 of the second opening 15b was set between 0.2 mm and 0.5 mm.

When the test liquid L3 remaining in the first fluid channel 14 migrates toward the absorption port 13 to allow the residual liquid-absorbing member 19 to absorb the test liquid L3, the amount of the test liquid L3 held in the second fluid channel 15 decreases from the given amount upon migration of the test liquid L in the first fluid channel 14. However, such a decrease can be prevented via the provision of a level difference at the first opening 15 as practiced in this embodiment. Also, the provision of a level difference at the second opening 15b enables secure retention of the test liquid L3 in the second fluid channel 15 and accurate measurement without exudation of liquid to the outside of the second opening.

Figure 17:
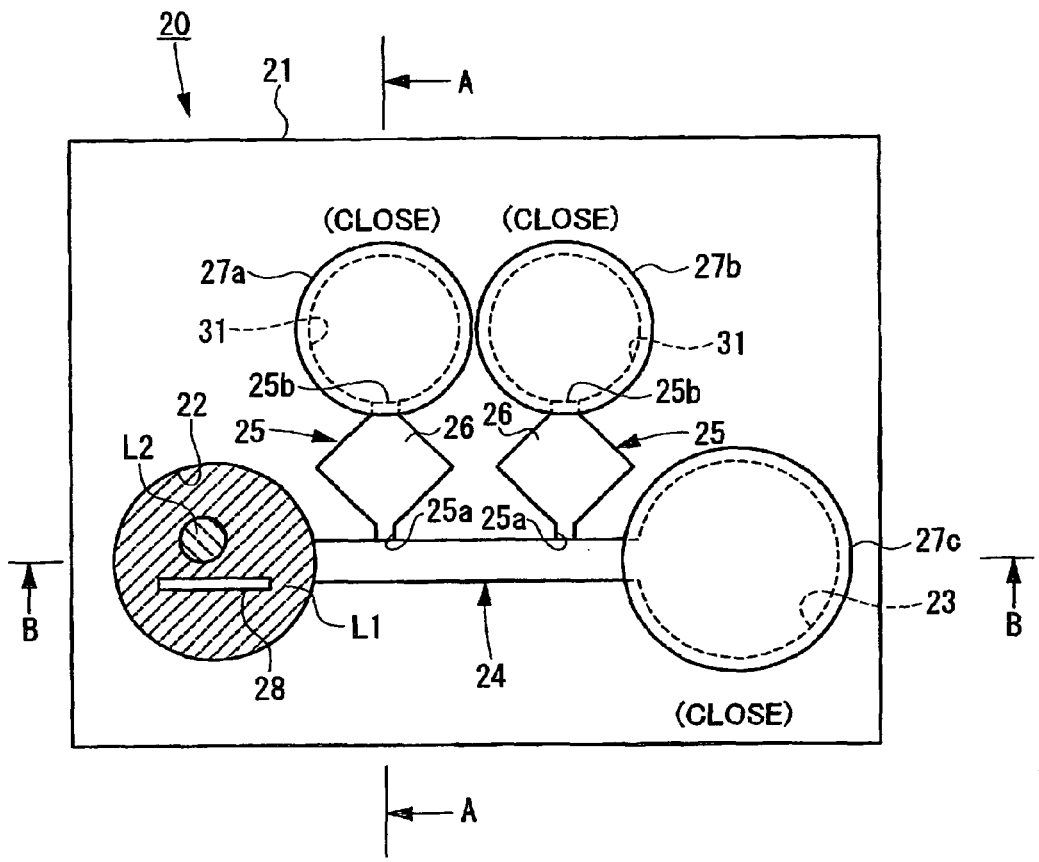
FIG. 17 shows the structure of the measuring chip according to the second embodiment.
Figure 18:
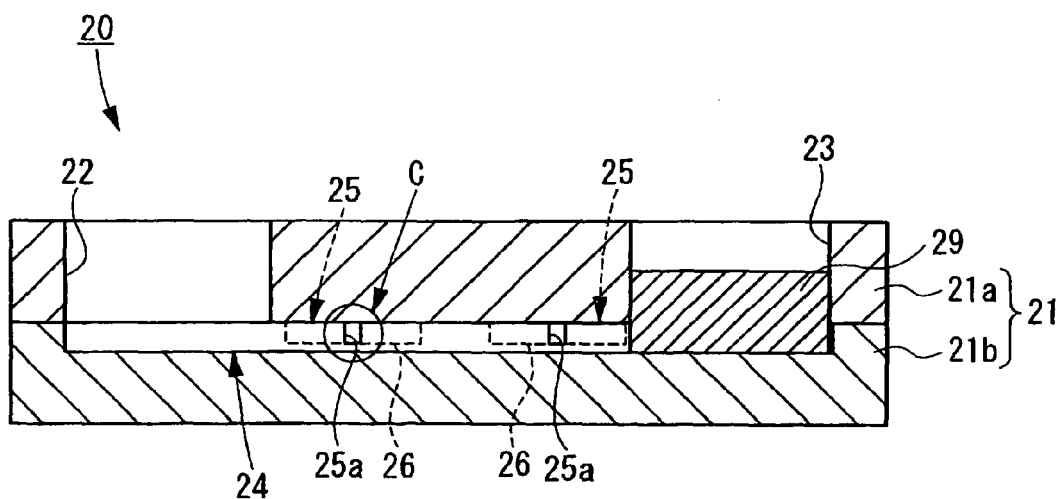
FIG. 18 is a cross sectional view as taken along section B-B of the measuring chip shown in FIG. 17.
Figure 19:
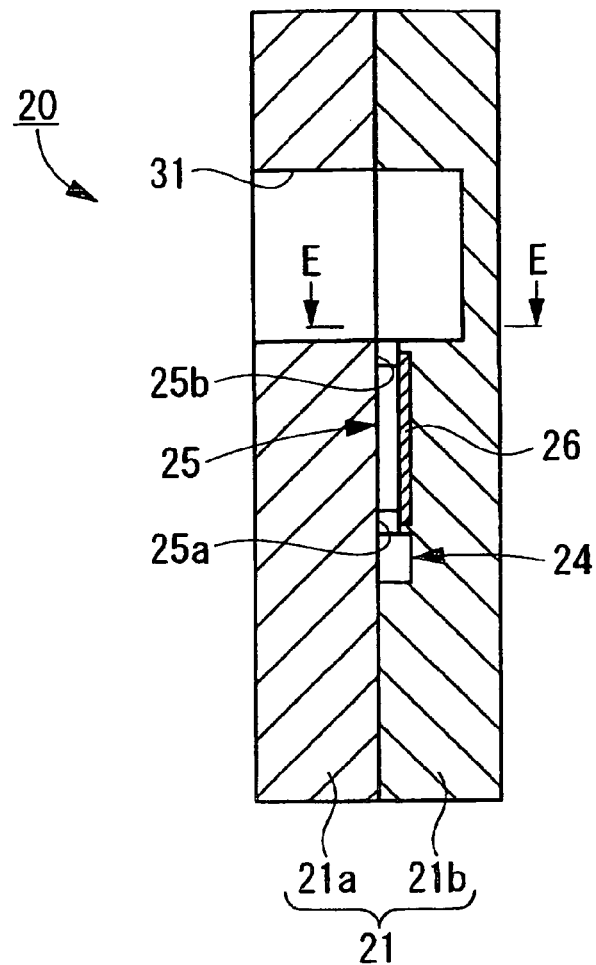
FIG. 19 is a cross sectional view as taken along section A-A of the measuring chip shown in FIG. 17.
Figure 20:
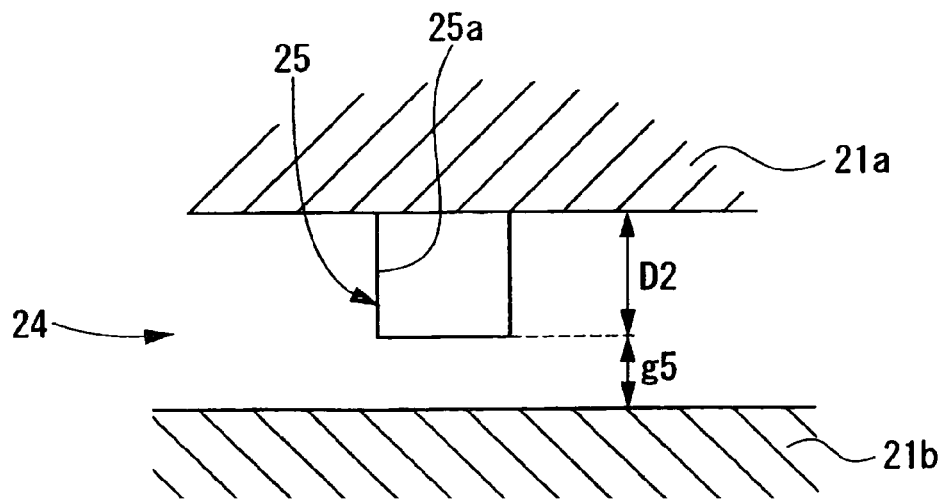
FIG. 20 is an enlarged view of "C" indicated by an arrow in FIG. 18.
Figure 21:
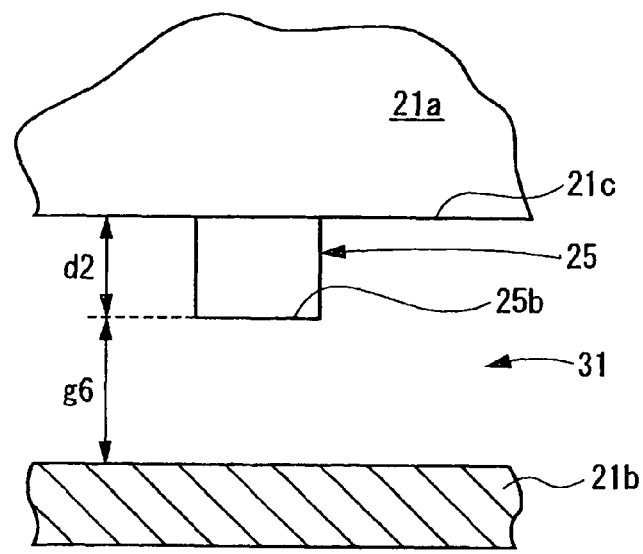
FIG. 21 is a cross sectional view as taken along section E-E of FIG. 19.
Figure 22:
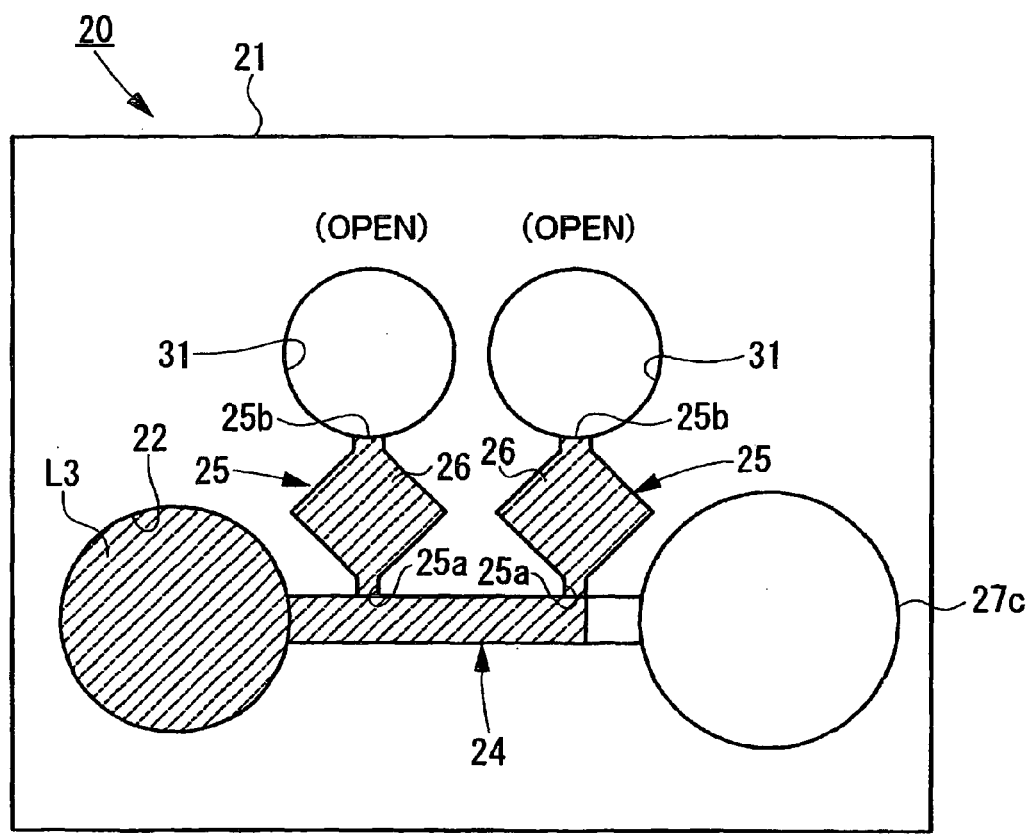
FIG. 22 illustrates the operations of the measuring chip according to the second embodiment.
Figure 23:
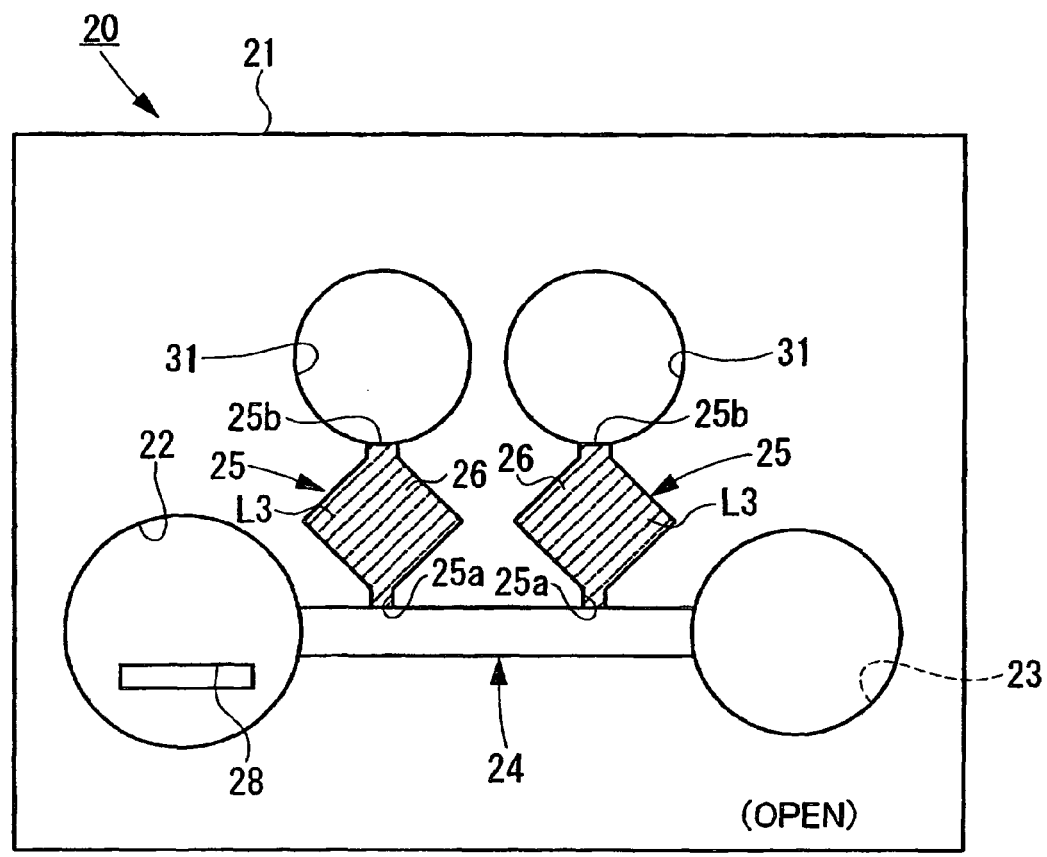
FIG. 23 illustrates the operations of the measuring chip according to the second embodiment.

The second embodiment of the measuring chip according to the present invention is described below. FIG. 17 shows the structure of the measuring chip according to the second embodiment. FIG. 18 is a cross sectional view as taken along section B-B of the measuring chip shown in FIG. 17. FIG. 19 is a cross sectional view as taken along section A-A of the measuring chip shown in FIG. 17. FIG. 20 is an enlarged view of "C" indicated by an arrow in FIG. 18. FIG. 21 is a cross sectional view as taken along section E-E of FIG. 19. FIG. 22 and FIG. 23 illustrate the operations of the measuring chip according to the second embodiment. In the embodiments described below, descriptions concerning members and the like having configurations and functions equivalent to those of the members and the like that have been described above are simplified or omitted by applying the same or equivalent symbols in the drawings.

A measuring chip 20 comprises a chip body 21. The chip body 21 is composed of a laminate of chip substrates 21a and 21b.

The chip body 21 comprises an agitation port 22 and an absorption port 23. The chip substrate 21b comprises the first fluid channel 24 in communication with the agitation port 22 at one of its ends and in communication with the absorption port 23 at the other end.

The agitation port 22 comprises a rotatable bar-like agitation member 28 for agitating the diluent L1 and the blood L2 that have been introduced. The absorption port 23 comprises a residual liquid-absorbing member 29.

The chip body 21 comprises a plurality of air-bleed ports 31 (2 ports in this embodiment). The second fluid channel 25 capable of measurement is provided between an air-bleed port 31 and a first fluid channel 24. As shown in the top view of the chip body 21 (the front elevational view of FIG. 17), a second fluid channel 25 is an approximately rectangular space.

A second fluid channel 25 comprises at one of its ends a first opening 25a in communication with the first fluid channel 24 and at the other end a second opening 25b in communication with the air-bleed port 31. In the present embodiment, the air-bleed port 31 functions as a third fluid channel. The number of the second fluid channels 25 and that of the air-bleed ports 31 are not particularly limited, and such numbers can be adequately altered in accordance with the number of times of testing or a type of testing.

A second fluid channel 25 comprises, at its bottom, a reaction member 26. A reaction member equivalent to one used in the above embodiment can be used as the reaction member 26. An example thereof is a slide for coloring reaction.

When the test liquid is not allowed to flow, for example, a case other than the testing, openings of the air-bleed ports 31 and of the absorption ports 23 are shielded with shield members 27a, 27b, and 27c.

As shown in FIG. 20, the first opening 25a of the second fluid channel 25 opens at the position of a gap g5 upwardly away from the bottom of the first fluid channel 24 (the top surface of the chip substrate 21b in FIG. 20). Thus, the peripheral portions of the left, the right, and the bottom of the first opening 25a are provided with level differences. This can prevent the test liquid L3 that has been once held in the second fluid channel 25 from leaking upon migration of the test liquid L in the first fluid channel 24. Further, it is preferable that the upper side of the first opening 25a opens at the position downwardly away from the top surface of the first fluid channel 24 (the bottom surface of the chip substrate 21a in FIG. 20). Thus, the test liquid L3 reservoired in the second fluid channel 25 can be more securely held.

It is preferable that the perimeter of the first opening 25a provided with a level difference be at least a half of the total perimeter of the first opening. If the first opening 25a is a D2×D2 square, for example, the perimeter provided with a level difference is represented by 3×D2, and the total perimeter of the first opening is represented by 4×D2.

As shown in FIG. 21, the second opening 25b of the second fluid channel 25 opens at the position of a gap g6 upwardly away from the bottom surface (the top surface of the chip substrate 21b in FIG. 21) of the air-bleed port 31 (the third fluid channel). Thus, the peripheral portions of the left, the right, the top and bottom of the second opening 25b are provided with level differences. This can prevent the test liquid L3 from exuding to the outside of the second opening, and such liquid can be securely held.

It is preferable that the perimeter of the second opening 25b provided with a level difference be at least a half of the total perimeter of the second opening. In the present embodiment, the second opening 25b is a d2×d2 square, and the perimeter provided with a level difference is represented by d2×4, which is equal to the total perimeter. This can prevent the test liquid L3 that is reservoired in the second fluid channel 25 from exuding toward the air-bleed port 31, and such liquid can be securely held.

In the measuring chip 20 according to the present embodiment, when the perimeter and the cross-sectional area of the vicinity of an opening 25a of the first fluid channel 24 in communication with the second fluid channel 25 are designated as L1 and S1, respectively, and the perimeter and the cross-sectional area of the first opening of the second fluid channel 25 are designated as L2 and S2, respectively, then the formula (L1/S1)<(L2/S2) is satisfied. The diameter of the first opening and that of the second opening may be set identical to those employed in the above embodiments.

Hereafter, operations of the measuring chip of the present embodiment are described.

At the outset, the air-bleed ports 31 are shielded with shield members 27a and 27b, and the absorption port 23 is shielded with a shield member 27c, as shown in FIG. 17. The diluent L1 and the blood L2 are introduced into the agitation port 22, and an agitation member 28 is driven to mix these two liquids via agitation with a stirrer. Thus, the test liquid L3 is generated.

As shown in FIG. 22, when an outlet of the agitation port 22 opens, the test liquid L3 flows through the first fluid channel 24, and the test liquid is introduced into the second fluid channels 25 capable of measurement with the effect of capillarity. Subsequently, when the absorption port 23 is opened, the test liquid L3 remaining in the first fluid channel 24 migrates toward the absorption port 23, and the liquid is entirely absorbed by a residual liquid-absorbing member 29 with the effect of capillarity, as shown in FIG. 23. Thus, a given amount of the test liquid L3 is held selectively in the second fluid channel 25.

The test liquid L3 held in the second fluid channel 25 develops color with the reaction member 26 provided in the second fluid channels 25. At this time, the absorbance of the reaction member 26 is measured to analyze a concentration of a specific substance.

The configuration of the measuring chip 20 according to the present embodiment eliminates the need for transporting the test liquid L3 after the measurement thereof in the second fluid channel 25, and thus, no residual liquid is generated. Since the measurement accuracy depends on the dimensional accuracy of the second fluid channel 25, the preparation of highly accurate microchips enables the highly accurate measurement.

Figure 24:
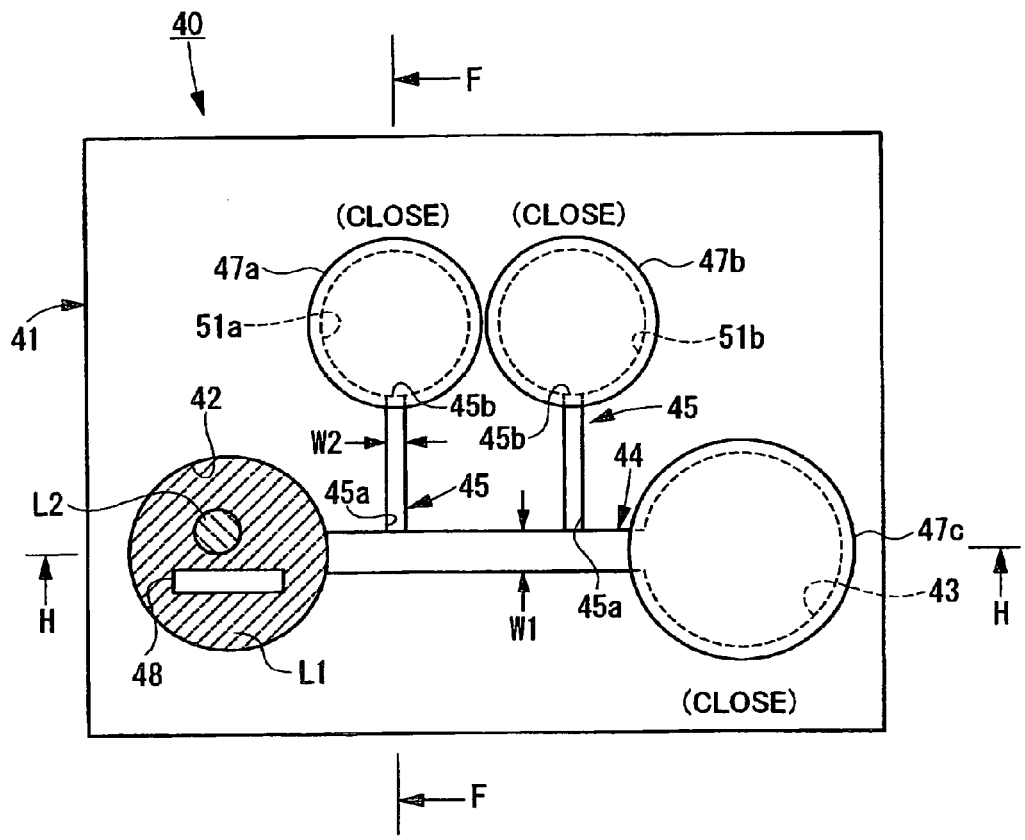
FIG. 24 shows the structure of the measuring chip according to the third embodiment.
Figure 25:
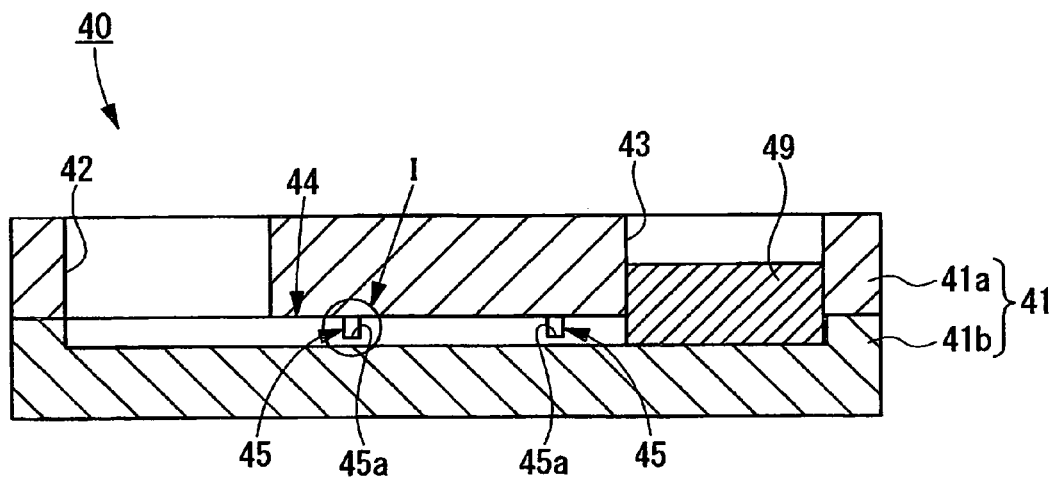
FIG. 25 shows a cross sectional view as taken along section H-H of the measuring chip shown in FIG. 24.
Figure 26:
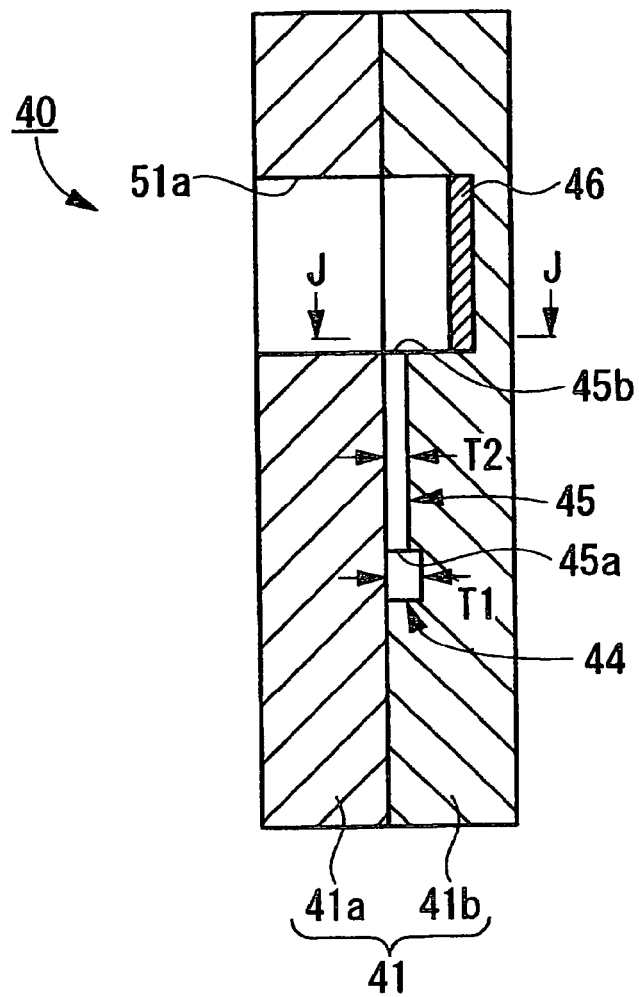
FIG. 26 shows a cross sectional view as taken along section F-F of the measuring chip shown in FIG. 24.
Figure 27:
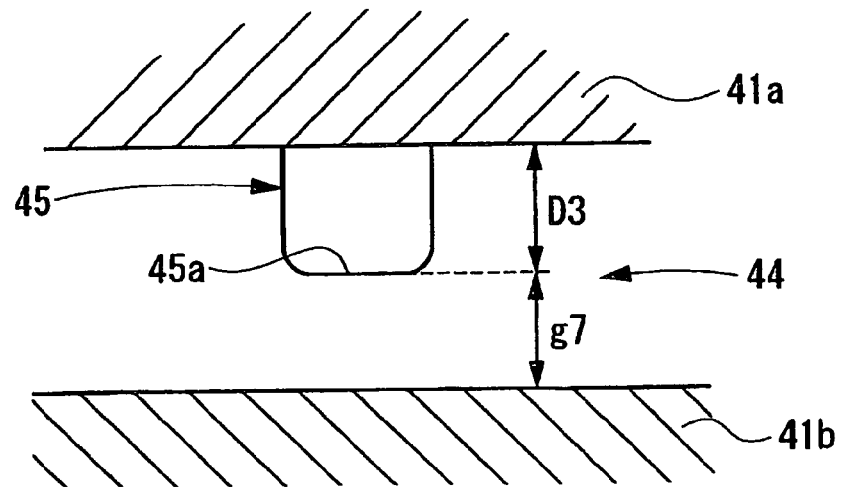
FIG. 27 is an enlarged view of "I" indicated by an arrow in FIG. 25.
Figure 28:
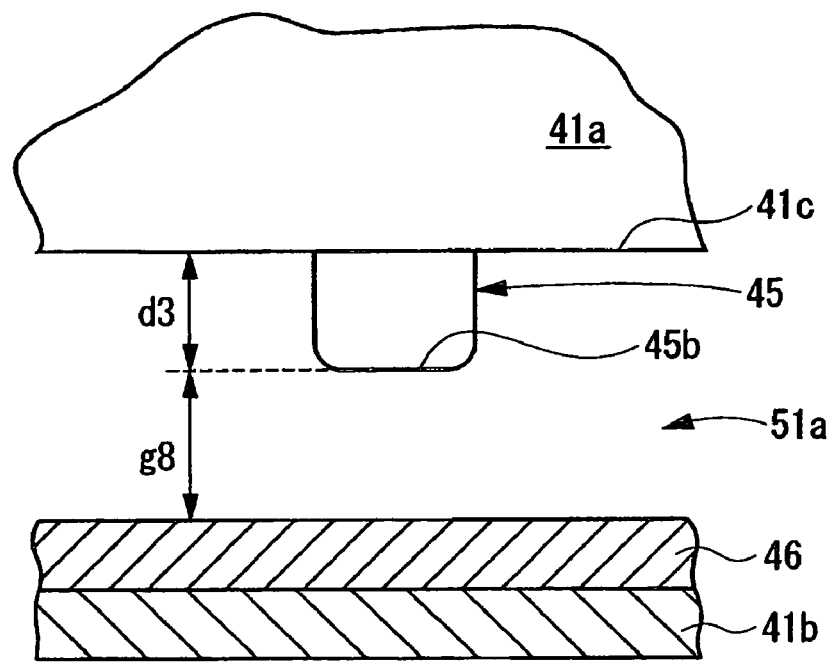
FIG. 28 is a cross sectional view as taken along section J-J of the measuring chip shown in FIG. 26.
Figure 29:
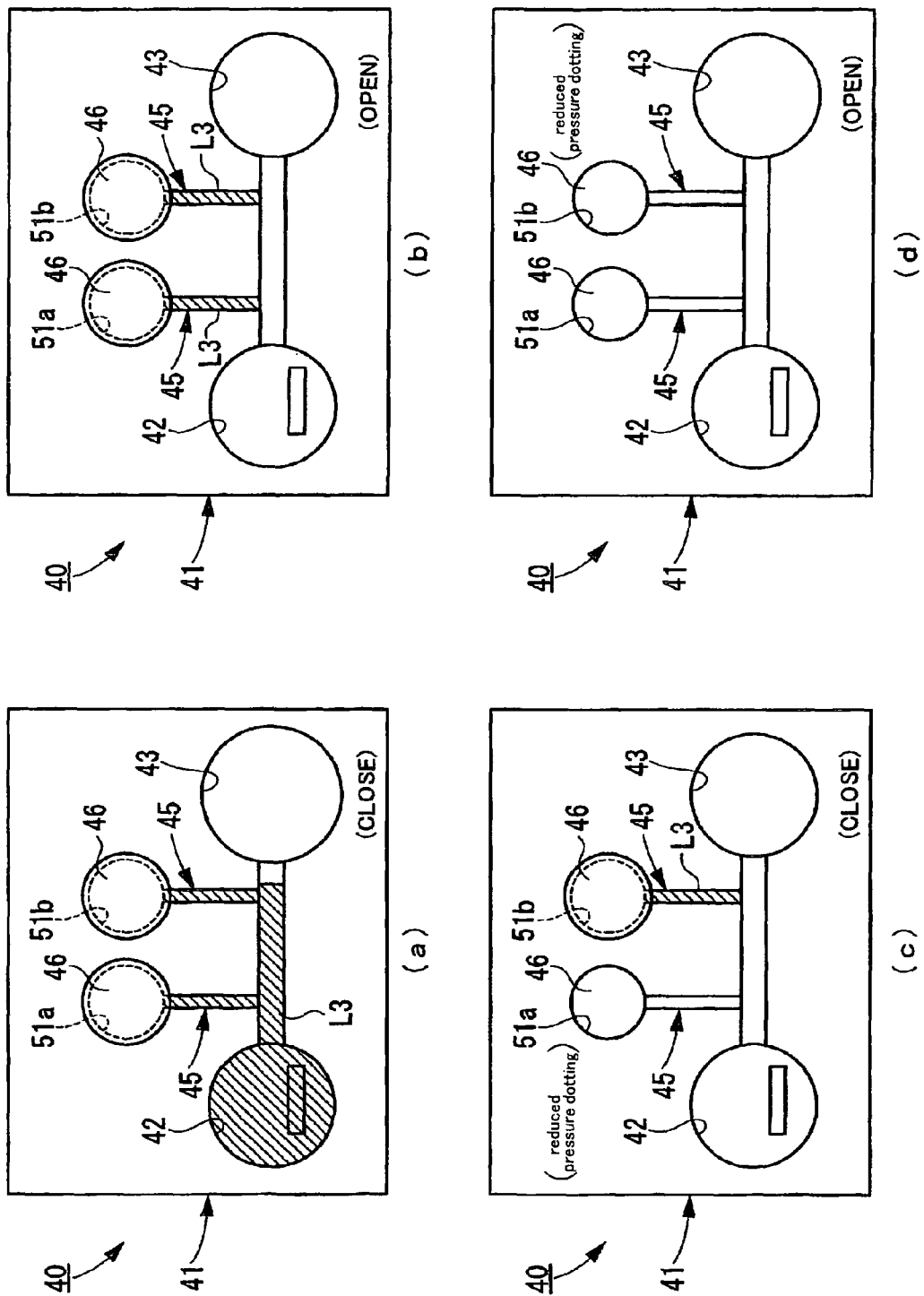
FIG. 29 illustrates the operations of the measuring chip according to the third embodiment.

The measuring chip according to the third embodiment of the present invention is described below. FIG. 24 shows the structure of the measuring chip according to the third embodiment. FIG. 25 shows a cross sectional view as taken along section H-H of the measuring chip shown in FIG. 24. FIG. 26 shows a cross sectional view as taken along section F-F of the measuring chip shown in FIG. 24. FIG. 27 is an enlarged view of "I" indicated by an arrow in FIG. 25. FIG. 28 is a cross sectional view as taken along section J-J of the measuring chip shown in FIG. 26. FIG. 29 illustrates the operations of the measuring chip according to the third embodiment. In the embodiments described below, descriptions concerning members and the like having configurations and functions equivalent to those of the members and the like that have been described above are simplified or omitted by applying the same or equivalent symbols in the drawings.

A measuring chip 40 comprises a chip body 41. The chip body 41 is composed of a laminate of chip substrates 41a and 41b.

The chip body 41 comprises an agitation port 42 and an absorption port 43. The chip substrate 41b comprises the first fluid channel 44 in communication with the agitation port 42 at one of its ends and in communication with the absorption port 43 at the other end.

The agitation port 42 comprises a rotatable bar-like agitation member 48 for agitating the diluent L1 and the blood L2 that have been introduced. The absorption port 43 comprises a residual liquid-absorbing member 49.

The chip body 41 comprises a plurality of air-bleed ports 51a and 51b (2 ports in this embodiment). The second fluid channel 45 capable of measurement is provided between an air-bleed port 51a or 51b and a first fluid channel 44.

A second fluid channel 45 comprises at one of its ends a first opening 45a in communication with the first fluid channel 44 and at the other end a second opening 45b in communication with the air-bleed port 51a or 51b. In the present embodiment, the air-bleed port 51a or 51b functions as a third fluid channel.

As shown in FIG. 26, the measuring chip 40 of the present embodiment comprises, at the bottoms of the air-bleed ports 51a and 51b, reaction members 46. Thus, the air-bleed ports 51a and 51b can also serve as spot-deposition sections. The number of the second fluid channels 45 and that of the air-bleed ports 51a and 51b are not particularly limited, and such numbers can be adequately altered in accordance with the number of times of testing or a type of testing. A reaction member equivalent to one used in the above embodiment can be employed as a reaction member 46. An example thereof is a slide for coloring reaction.

When the test liquid is not allowed to flow, for example, a case other than the testing, openings of the air-bleed ports 51a and 51b and of the absorption port 43 are shielded with shield members 47a, 47b, and 47c.

As shown in FIG. 27, the first opening 45a of the second fluid channel 45 opens at the position of a gap g7 upwardly away from the bottom of the first fluid channel 44 (the top surface of the chip substrate 41b in FIG. 27). Thus, the peripheral portions of the left, the right, and the bottom of the first opening 45a are provided with level differences. This can prevent the test liquid L3 that has been once held in the second fluid channel 45 from leaking upon migration of the test liquid L in the first fluid channel 44. Further, it is preferable that the upper side of the first opening 45a open at the position downwardly away from the top surface of the first fluid channel 44 (the bottom surface of the chip substrate 41a in FIG. 20). Thus, the test liquid L3 reservoired in the second fluid channel 45 can be more securely held.

It is preferable that the perimeter of the first opening 45a provided with a level difference be at least a half of the total perimeter of the first opening. If the first opening 45a is a D3×D3 square, for example, the perimeter provided with a level difference is represented by 3×D3, and the total perimeter of the first opening is represented by 4×D3.

As shown in FIG. 28, the second opening 45b of the second fluid channel 45 opens at the position of a gap g8 upwardly away from the top surface of the reaction member 46 disposed at the bottom surface of the air-bleed port 51a (the third fluid channel). Thus, the peripheral portions of the left, the right, top and the bottom of the second opening 45b are provided with level differences. This can prevent the test liquid L3 reservoired in the second fluid channel 45 from exuding toward the air-bleed port, such liquid can be securely held, and accurate measurement can be performed.

It is preferable that the perimeter of the second opening 45b provided with a level difference be at least a half of the total perimeter of the second opening. In the present embodiment, the second opening 45b is a d3×d3 square, the perimeter thereof is represented by d3×4, and the perimeter provided with a level difference is represented by d3×4. This can prevent the test liquid L3 that is reservoired in the second fluid channel 45 from exuding toward the air-bleed ports 51a and 51b, such liquid can be securely held, and accurate measurement can be performed.

In the measuring chip 40 according to the present embodimentm, when the perimeter and the cross-sectional area of the vicinity of a first opening 45a of the first fluid channel 44 in communication with the second fluid channel 45 are designated as L1 and S1, respectively, and the perimeter and the cross-sectional area of the first opening 45a of the second fluid channel 45 are designated as L2 and S2, respectively, then the formula (L1/S1)<(L2/S2) is satisfied. This can prevent the test liquid L3 held in the second fluid channel 45 from flowing backward to exude into the first fluid channel 44 at the time of removal of residual liquid from the first fluid channel 44. The diameter of the first opening and that of the second opening may be the same as those employed in the above embodiments.

Figure 30:
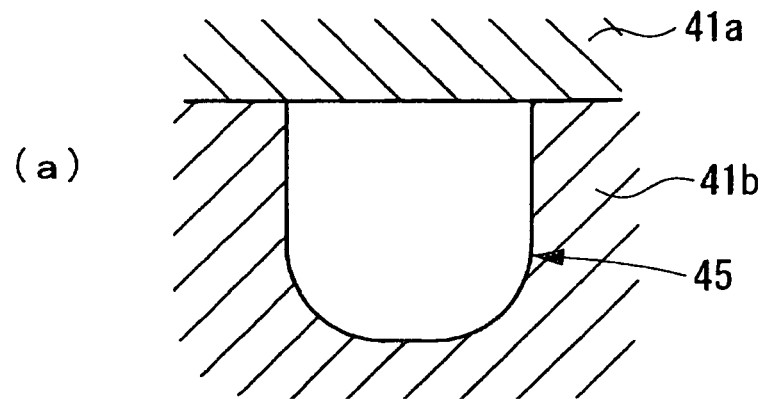
FIG. 30 is a cross sectional view showing an example of a modified bottom surface of the second fluid channel.
Figure 30:
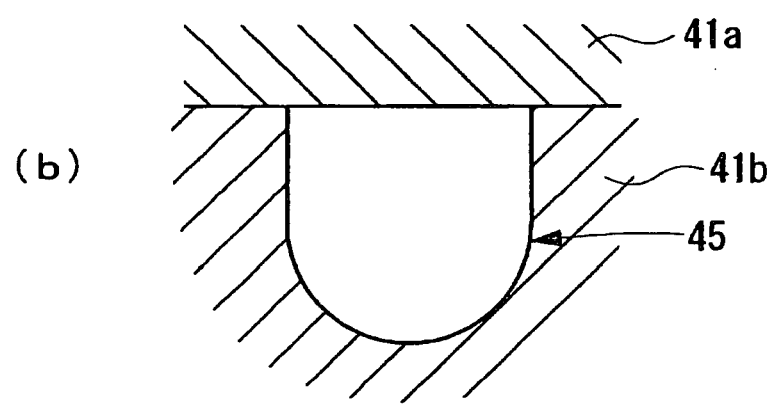
Figure 30:
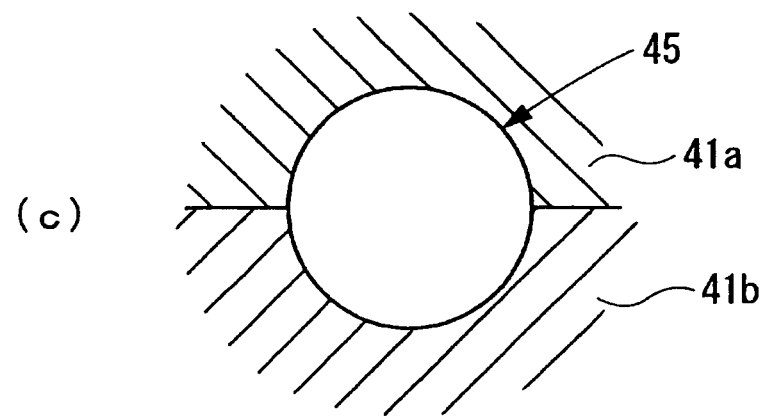

As shown in FIG. 30(a) to (c), the bottom of the second fluid channel in the measuring chip 40 of the present embodiment is preferably round-cornered in order to minimize the amount of the residual liquid in the second fluid channel 45 at the time of transportation of the test liquid after measuring. As shown in FIG. 30(a), the liquid remaining can be suppressed by selectively rounding the corner of the bottom of the second fluid channel 45. As shown in FIG. 30(b), the liquid remaining can be more assuredly suppressed by preparing a completely round bottom. As shown in FIG. 30(c), the top surface (the lower surface of the chip substrate 41a in FIG. 30(c)) may be rounded as well as the bottom surface to prepare the second fluid channel 45 with an approximately circular shape via a cross-sectional observation. As in the case of the present embodiment, the bottoms of the second fluid channels 25 and 45 capable of measurement are preferably rounded in the second embodiment above.

Hereafter, operations of the measuring chip of the present embodiment are described.

First, the air-bleed ports 51a and 51b are shielded with shield members 47a and 47b, and the absorption port 43 is shielded with a shield member 47c, as shown in FIG. 24. The diluent L1 and the blood L2 are introduced into the agitation port 42, and an agitation member 48 is driven to mix these two liquids via agitation with a stirrer. Thus, the test liquid L3 is generated.

As shown in FIG. 29(a), when an outlet of the agitation port 42 opens, the test liquid L3 flows through the first fluid channel 44, and the test liquid is introduced into the second fluid channels 45 that functions as measuring capillaries with the effect of capillarity. Subsequently, when the absorption port 43 is opened, the test liquid L3 remaining in the first fluid channel 44 migrates toward the absorption port 43, and the liquid is entirely absorbed by a residual liquid-absorbing member 49 with the effect of capillarity, as shown in FIG. 29(b). Thus, a given amount of the test liquid L3 is held selectively in the second fluid channel 45.

As shown in FIG. 29(c), selective depressurization of the air-bleed port 51a induces the introduction of the test liquid L3, which is held in the second fluid channel 45 in communication with the air-bleed port 51a, into the air-bleed port 51a. As shown in FIG. 29(d), depressurization of the air-bleed port 51b induces the introduction of the test liquid L3, which is held in the second fluid channel 45 in communication with the air-bleed port 51b, into the air-bleed port 51b. Alternatively, the air-bleed ports 51a and 51b may be simultaneously subjected to depressurization to perform spot-deposition.

The test liquids L3 that have been introduced into the air-bleed ports 51a and 51b bring about color development with reaction members 46 provided in the air-bleed ports 51a and 51b. At this time, the absorbance of the reaction member 46 is measured to analyze the concentration of a specific substance.

As shown in FIG. 26, the measuring chip 40 of the present embodiment is preferably configured in a manner such that the top surface of the first fluid channel 44 that functions as a communication capillary and the top surface of the second fluid channel 45 that functions as a measuring capillary are present on the same planar surface (the boundary between the chip surfaces 41a and 41b), and the depth T2 of the second fluid channel 45 is shallower than the depth T1 of the first fluid channel 44.

The pressure resistance at cross section of the measuring chip 40 of the present embodiment (perimeter×liquid surface tension/cross-sectional area) is larger than the pressure resistance at cross section of the first fluid channel 44. That is, the correlation represented by the following formula is attained.

$$2(W2+T2)\cdot\gamma/(W2\cdot T2) > 2(W1+T1)\cdot\gamma/(W1\cdot T1)$$

In the present embodiment, the test liquid was spot-deposited via depressurization; however, the test liquid can be spot-deposited via pressurization from the upstream.

As shown in FIG. 26, the measuring chip 40 of the present embodiment is constructed in a manner such that the bottom surface of the second fluid channel 45 (the right side in FIG. 26) is not present on the same planer surface with the top surface of the reaction member 46 of the air-bleed ports 51a or 51b (the left side in FIG. 26).

The present invention will be described in more detail by referring to the following examples. However, the present invention is not limited thereto.

EXAMPLES

Example 1

Saturated Water Absorption of Various Types of Porous Materials with Respect to a Liquid and the Precision Thereof (1) A Method for Producing a Multilayer Dry Analysis Element Using a Textile as a Porous Material Used for Weighing An aqueous solution of the following composition was coated to a colorless transparent polyethylene terephthalate film (180 μm thick) undercoated with gelatin. Then, the film was dried.

| | |
|---|---|
| Gelatin | 16.6 g/m$^2$ |
| Polyoxy(2-hydroxyl)poropyrenenonyphenylether | 0.2 g/m$^2$ |

Then, water was supplied to the entire surface of the aforementioned film in an amount of about 30 g/m$^2$ such that the film became wet. Then, a 36-gauge tricot textile (hereafter to be referred to as "textile") of polyethylene terephthalate spun yarn (equivalent to a 50 denier fabric) was laminated to the film by lightly applying pressure in a virtually uniform manner so as to prepare a porous material layer (textile layer). The film was dried so as to be bound together with the layer. The aforementioned multilayer dry analysis element was cut into 12 mm×13 mm chips so as to obtain a slide 1 used for weighing experimentation.

(2) A Method for Producing a Multilayer Dry Analysis Element Using a Polymer Porous Membrane as a Porous Material Used for Weighing An aqueous solution of the following composition was coated to a colorless transparent polyethylene terephthalate film (180 μm thick) undercoated with gelatin. Then, the film was dried.

| | |
|---|---|
| Gelatin | 16.6 g/m$^2$ |
| Polyoxy (2-hydroxyl)poropyrenenonyphenylether | 0.2 g/m$^2$ |

Then, water was supplied to the entire surface of the film in an amount of about 15 g/m$^2$ such that the film became wet. Then, a polysulfone membrane (SE-200: Fujifilm; hereafter to be referred to as "PS membrane") was laminated to the film by lightly applying pressure. The film was dried so as to be bound together with the membrane. Thus, a multilayer dry analysis element was produced using a polysulfone membrane as a porous material used for weighing. The aforementioned multilayer dry analysis element was cut into 12 mm×13 mm chips so as to obtain a slide 2 used for weighing experiments.

(3) Saturated Water Absorption of Various Types of Porous Materials with Respect to a Liquid and the Precision Thereof A liquid (10 ppm dye aqueous solution) was supplied to a slide 1 using a fiber of Kimwipe paper by the method shown in FIG. 1(b). A change in the weight of the slide was measured by a precision balance (Mettler Toledo). The weight of the slide increased along with the length of liquid supply time, and the slide became saturated in 2 minutes (FIG. 2). The saturated water absorption of the textile was about 55 μl. Further, the precision of saturated water absorption of the textile (coefficient of variation (CV) (%); n=10) was calculated (Table 1). The weighing precision of the textile in terms of an aqueous solution was found to be less then 1%.

Using the method described above, the saturated water absorption of a slide 2 and the precision thereof were determined. The results are shown in Table 1. The saturated water absorption of a PS membrane was about 27.5 μl. The precision of saturated water absorption of a PS membrane was about 1.4%.

TABLE 1

Weighing precision based on the saturated water absorption of a porous material textile and that of a PS membrane

| Number of Times for Weighing | Water Absorption (g) | |
|---|---|---|
| | Textile | PS Membrane |
| 1 | 0.0554 | 0.0271 |
| 2 | 0.0548 | 0.0283 |
| 3 | 0.0555 | 0.0275 |
| 4 | 0.0551 | 0.0274 |
| 5 | 0.0552 | 0.0273 |
| 6 | 0.0552 | 0.0272 |
| 7 | 0.0539 | 0.0277 |
| 8 | 0.0553 | 0.0279 |
| 9 | 0.0555 | 0.0272 |
| 10 | 0.0559 | 0.0272 |
| Mean Value | 0.05518 | 0.02748 |
| SD | 0.000535 | 0.000382 |
| CV (%) | 0.969549 | 1.391522 |

Example 2

Quantitative Experimentation Using a Multilayer Dry Analysis Element Comprising a Porous Material as a Weighing Layer (1) A Method for Producing a Multilayer Dry Analysis Element for CRP Analysis as a Weighing Layer (Textile)

A reagent solution containing a cross-linking agent of the following content was coated to a colorless transport polyethylene terephthalate film (180 μm thick) undercoated with gelatin such that the film was covered therewith. Then, the film was dried. Thus, a reagent layer was provided to the film.

| Alkali-treated gelatin | 14.5 g/m² |
|---|---|
| Nonylphenoxypolyethoxyethanol | 0.2 g/m² |
| (average content of oxyethylene: 9 to 10 units) | |
| Glucose oxidase | 5000 U/m² |
| Peroxidase | 15000 U/m² |
| Glucoamylase | 5000 U/m² |
| 2-(4-hydroxy-3,5-dimetoxyphenyl-4-[4-(dimethylamino)phenyl]-5-phenethylimidazole (leuco dye) acetate | 0.38 g/m² |
| Bis[(vinylsulfonylmethylcarbonyl)amino]methane | 0.1 g/m² |

An adhesive layer of the following content was coated to the reagent layer such that the film was covered therewith. Then, the film was dried. Thus, the adhesive layer was provided to the film.

| Alkali-treated gelatin | 14.5 g/m² |
|---|---|
| Bis[(vinylsulfonylmethylcarbonyl)amino]methane | 0.1 g/m² |

Then, an aqueous solution containing the following reagents of the following content was applied to the surface of the adhesive layer such that the layer was coated with therewith. The gelatin layer was allowed to become swollen. Thereafter, a 36-gauge tricot textile of polyethylene terephthalate (PET) spun yarn (equivalent to a 50 denier fabric, about 250 μm thick) was laminated onto the film by lightly applying pressure in a virtually uniform manner. Thus, a porous development layer (textile layer) was provided to the film.

| Nonylphenoxypolyethoxyethanol | 0.15 g/m² |
|---|---|
| (average content of oxyethylene: 9 to 10 units) | |
| Bis[(vinylsulfonylmethylcarbonyl)amino]methane | 0.4 g/m² |

Then, a substrate of the following content was coated to the porous development layer such that the layer was coated therewith. Then, the film was dried. Thus, a multilayer analysis element for CRP analysis was prepared.

| Carboxymethylated starch | 5 g/m² |
|---|---|
| Nonylphenoxypolyethoxyethanol | 0.2 g/m² |
| (average content of oxyethylene: 9 to 10 units) | |

Further, an ethanol solution was coated to the tricot textile layer as a development and weighing layer such that the layer was covered with amylase-anti-CRP·IgG conjugate in an amount of 3 mg/m². The solution was allowed to impregnate such layer. Then, the film was dried. Thus, a multilayer dry analysis element for CRP analysis was obtained.

Subsequently, the aforementioned multilayer dry analysis element was cut into 12 mm×13 mm chips. The chips were fitted to slide frames disclosed in JP Patent Publication (Kokai) No. 57-63452 A (1982) so as to obtain multilayer dry slides for CRP analysis.

(Quantitative Examination)

Figure 3:
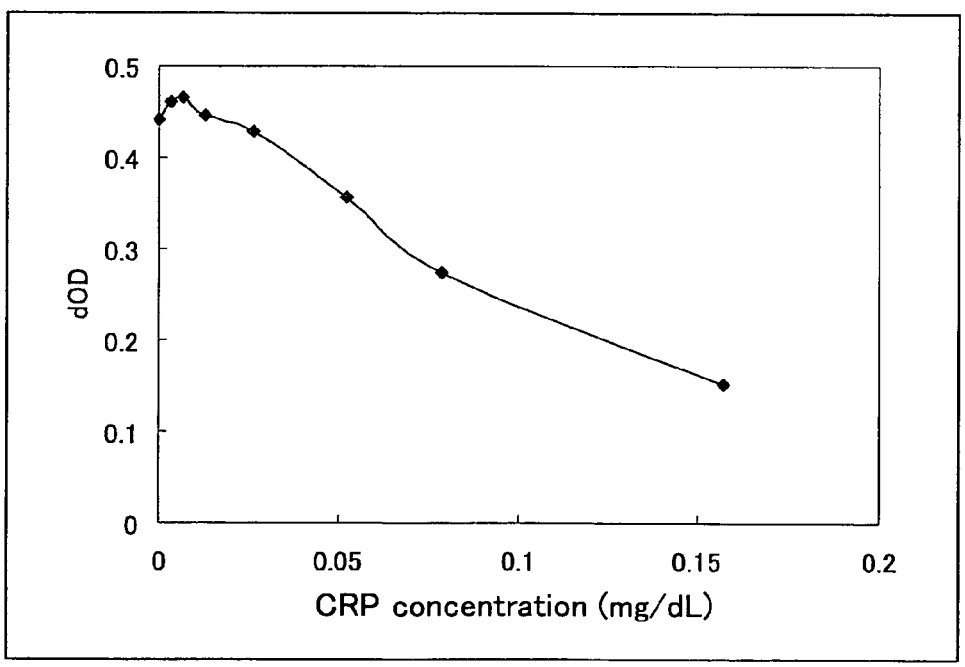
FIG. 3 shows a calibration curve of a CRP dry analysis element when the porous material layer used for weighing is a textile.

To the aforementioned CRP slide, 50 mM glycerophosphoric acid buffer solution (pH 7) containing a known amount of human CRP was supplied in an amount relating in saturated water absorption (55 μL) by method 4 (FIG. 1($d$)). The slide was kept at 37° C., and reflective photometric concentration was masured from the PET substrate side using visible light with the center wavelength at 650 nm. A calibration curve was created by calculating differences in reflective photometric concentrations at 3 and 5 minutes (ΔOD5-3) after initiation of the reaction. As shown in FIG. 3, it is obvious that CRP quantification can be carried out with good sensitivity by the weighing method of the present invention.

Example 3

Quantitativity of a Multilayer Dry Analysis Element in Which a Porous Material is used for Weighing in a Microchip System (1) Production of Concave-Shaped PDMS A silicon wafer was spin coated with thick film photoresist SU-8 so as to have a film thickness of 100 μm. The wafer was preheated at 90° C. for 1 hour and was irradiated with UV light via a mask on which a channel pattern I that corresponds to FIG. 4 had been drawn. Then, the irradiated area was cured at 90° C. for 1 hour. Thereafter, the non-cured area was dissolved using propylene glycol monomethyl ether acetate (PGMEA) so as to be removed. After being washed with water and dried, the wafer was used as a convex-shaped silicon wafer/SU8.

Figure 4:
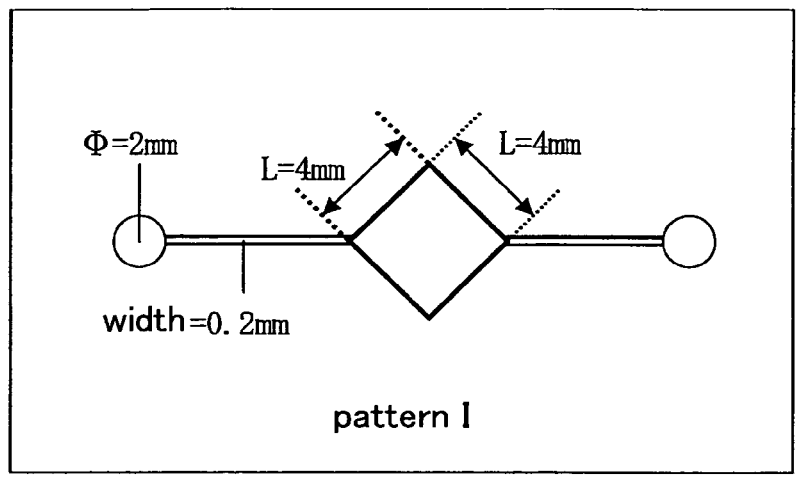
FIG. 4 shows concave-shaped PDMS patterns.
Figure 4:
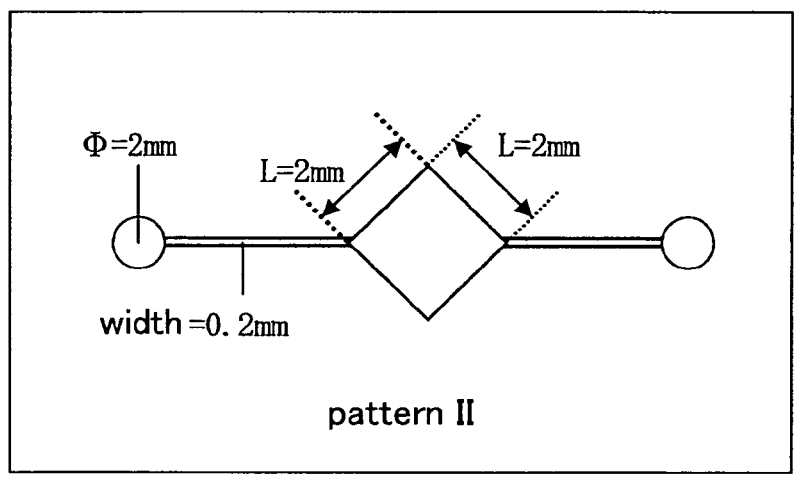

PDMS (a mixture of Dupont Sylgard and a curing liquid (the ratio of Dupont Sylgard to the curing liquid was 10:1)) was poured into the convex-shaped silicon wafer so as to be cured at 80° C. for 3 hours. The cured PDMS was carefully removed from the convex-shaped silicon wafer such that a concave-shaped PDMS pattern I as shown in FIG. 4 was produced. Further, a specimen inlet 1 and an air vent 2 (diameter: 1 mm) were created on the pattern using a disposable biopsy punch (*Seiken Torepan*; Kai Industries).

Subsequently, a concave-shaped PDMS pattern II was produced by the aforementioned method.

(2) Production of a Multilayer Dry Analysis Element for Glucose Analysis

Type 1 (glucose dehydrogenase (GDH) method): An aqueous solution with the following composition was coated to a smooth colorless transparent PET film (180 μm thick) undercoated with gelatin such that the film had the thickness of 40 μm after being dried, and was dried so as to provide a reaction layer.

| | |
|---|---|
| Alkali-treated gelatin | 20.0 g/m$^2$ |
| NTB | 0.8 g/m$^2$ |
| Surfactant | 0.8 g/m$^2$ |
| Diaphorase | 0.75 KU/m$^2$ |
| Acetone | 2.4 g/m$^2$ |

Here, the surfactant used was polyoxy(2-hydroxy)propylenenonylphenyl ether (surfactant 10 G, Olin). In addition, NTB indicates 3,3'-(3,3'-dimetoxy-4,4'-biphenylene)bis[2-(p-nitrophenyl)-5-phenyltetrazoliumchloride].

Then, an aqueous solution with the following composition was coated to the film such that the film contained the following components in their respective amounts. Thereafter, the film was dried. Thus, a dry analysis element for glucose analysis used in the type 1 method (GDH method) was produced.

| | |
|---|---|
| Alkali-treated gelatin | 14.5 g/m$^2$ |
| Nonylphenoxypolyethoxyethanol | 0.2 g/m$^2$ |
| (average content of oxyethylene: 9 to 10 units) | |
| Glucose dehydrogenase (GDH) | 5000 U/m$^2$ |
| NAD | 0.25 g/m$^2$ |
| Latex (40 μm) suspension | 25 ml/m$^2$ |
| Bis[(vinylsulfonylmethylcarbonyl)amino]methane | 0.1 g/m$^2$ |

Type 2 (glucose dehydrogenase (GOD) method): An aqueous solution with the following composition was coated to a smooth colorless transparent PET film (180 μm thick) undercoated with gelatin such that the film had a thickness of 40 μm after being dried, and was dried so as to provide a reaction layer.

| | |
|---|---|
| Alkali-treated gelatin | 20.0 g/m$^2$ |
| POD | 15.2 kU/m$^2$ |
| Methanol | 6.8 g/m$^2$ |
| Monopotassium phosphate | 0.46 g/m$^2$ |
| L-alanine | 2.82 g/m$^2$ |
| α-ketoglutaric acid.2Na | 0.48 g/m$^2$ |

| | |
|---|---|
| -continued | |
| 20% MgCl$_2$ | 1.22 g/m$^2$ |
| Pyruvate oxidase (POPG) | 3.45 kU/m$^2$ |
| 2-(3,5-dimetoxy-4-hydroxyphenyl)-4-[4-(dimethylamino)phenyl]-5-phenethylimidazole | 0.29 g/m$^2$ |
| 1N NaOH (pH = 7.5) | 0.49 g/m$^2$ |

Then, an aqueous solution with the following composition was coated to the film such that the film contained the following components in their respective amounts. Thereafter, the film was dried. Thus, a dry analysis element for glucose analysis used in the type 2 method (GOD method) was produced.

| | |
|---|---|
| Alkali-treated gelatin | 14.5 g/m$^2$ |
| Nonylphenoxypolyetoxy ethanol | 0.2 g/m$^2$ |
| (average content of oxyethylene: 9 to 10 units) | |
| glucose oxidase (GOD) | 5.0 kU/m$^2$ |

(3) Production of Microchip for Glucose Quantification

Figure 5:
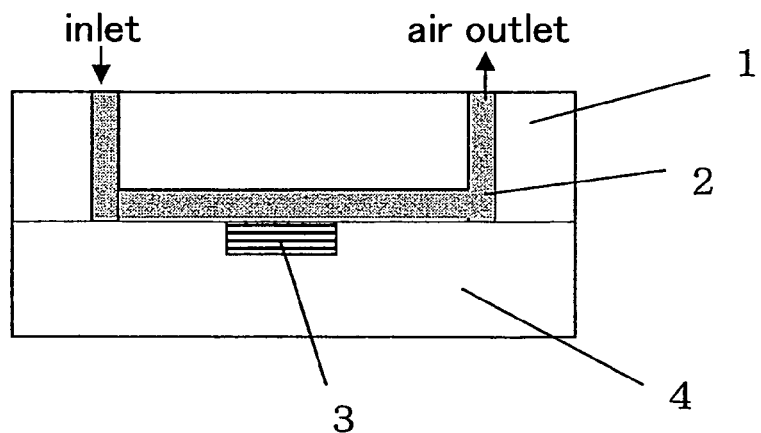
FIG. 5 shows a production of a microchip for glucose quantification. Numerical reference 1 denotes a concave-shaped PDMS, 2 denotes a channel, 3 denotes a dry analysis element for glucose quantification, and 4 denotes a PDMS sheet.

Concave-shaped PDMS patterns I and II produced in (1) were processed to have a size of 24 mm×12 mm. Then, the two types of dry analysis elements for glucose analysis produced in (2) were cut into 4 mm×4 mm chips and 2 mm×2 mm chips, respectively. Both types of chips were fitted to corresponding concave-shaped PDMS patterns that had been processed. Thus, microchips for glucose quantification were produced (FIG. 5).

(Quantitative Evaluation)

Measurement of glucose by a weight detection method using a porous material layer in a microchip (1) Creation of a Glucose Calibration Curve by GDH Method: (Large Cell Size: 4 mm×4 mm; Weighing Layer: Latex Particle/Gelatin Gel)

Figure 6:
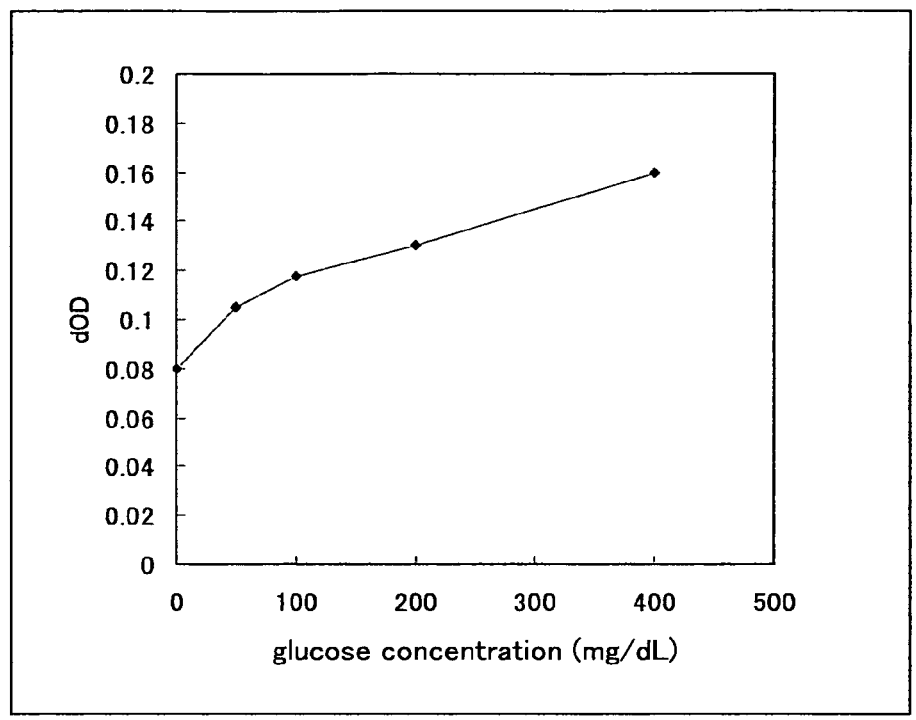
FIG. 6 shows a glucose calibration curve obtained using a latex-particle/gelatin layer inside of a microchip for weighing.

A glucose aqueous solution (50%; Otsuka Pharmaceutical Co., Ltd.) was diluted with 20 mM Tris-HCl buffer solution (pH 7.5) such that glucose aqueous solutions at different concentrations (0 mg/dL to 400 mg/dL) were prepared. Each glucose aqueous solution at each concentration was carefully injected via an inlet 1 of a microchip (concave-shaped PDMS pattern I) such that a cell at the center of the chip was filled with the solution. Each chip was subjected to transmission photometry at 540 nm using a light-scattering spectrophotometer (MCPD-2000; Otsuka Electronics Co., Ltd.) while being kept at 37° C. 5 minutes thereafter, transmission OD was calculated so as to create a calibration curve (FIG. 6). As indicated by the calibration curve shown in FIG. 6, it is obvious that glucose quantification can be performed in a microsystem with good precision by the weight detection method of the present invention.

(2) Creation of a Glucose Calibration Curve by GOD Method: (Small Cell Size: 2 mm by 2 mm; Weighing Layer: Gelatin Gel)

Figure 7:
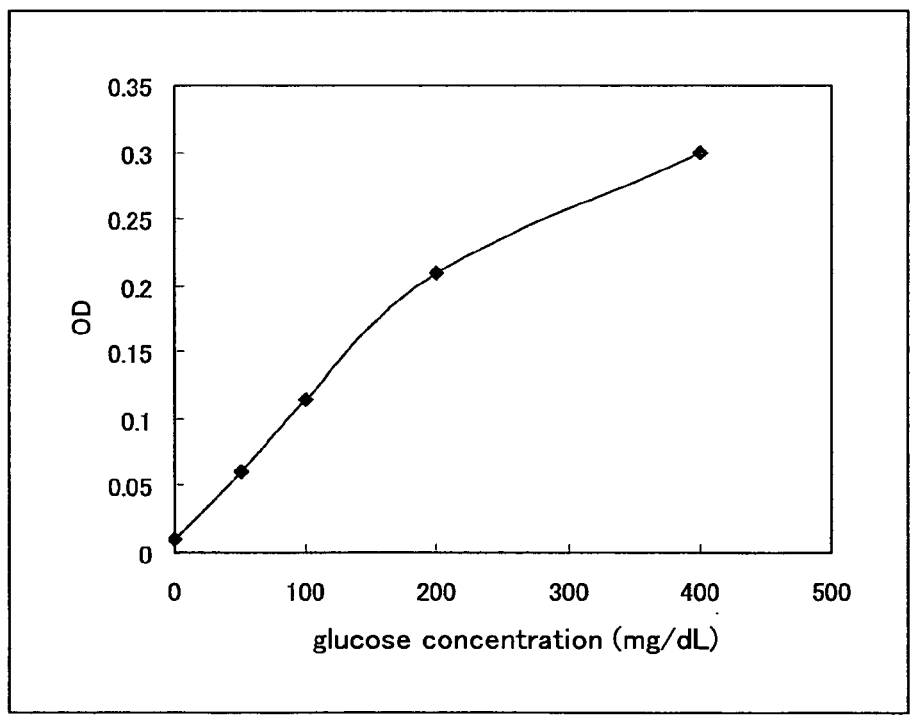
FIG. 7 shows a glucose calibration curve obtained using a gelatin layer inside of a microchip for weighing.

A glucose aqueous solution (50%; Otsuka Pharmaceutical Co., Ltd.) was diluted with 20 mM Tris-HCl buffer solution (pH 7.5) such that glucose aqueous solutions at different concentrations (0 mg/dL to 400 mg/dL) were prepared. Each glucose aqueous solution at each concentration was carefully injected via an inlet 1 of a microchip (concave-shaped PDMS pattern II) such that a cell at the center of each chip was filled with the solution. Each chip was subjected to transmission photometry at 505 nm using a light-scattering spectrophotometer (MCPD-2000; Otsuka Electronics Co., Ltd.) while being kept at 37° C. 5 minutes thereafter, transmission OD was calculated so as to create a calibration curve (FIG. 7). As indicated by the calibration curve shown in FIG. 7, it is obvious that glucose quantification can be performed in a microsystem with good precision by the weight detection method of the present invention.

Example 4

A round capillary measuring chip having the configuration of the measuring chip according to the first embodiment mentioned herein was evaluated in terms of accuracy.

At the outset, 1 µl of blood and 20 µl of a diluent were introduced into an agitation port 12. While an absorption port 13 and an outset were shielded, the liquids were mixed via agitation with a stirrer. After these liquids were homogenously mixed, the outlet was opened. Thus, the test liquid L3 passed through the communication capillary (i.e., the first fluid channel 14) with the effect of capillarity, and it was introduced into a plurality of round capillaries (i.e., the second fluid channels 15). The absorption port 13 was then opened, the liquid migrated toward the residual liquid-absorbing member 19 (i.e., a liquid-absorbing pad), and the residual liquids other than the liquid that had been introduced into the round capillary and measured were absorbed with the effect of capillarity of the liquid-absorbing pad. Thus, the mixed solution was measured and separated. The measured liquid was placed into a microtube under increased or reduced pressure to bring the content of the tube to 1 ml. The absorbance was measured with a spectrophotometer, and the measured value was converted into a volume using the calibration curve. As a result of the evaluation (N=20), the measurement and transportation accuracy of the round capillary measuring chip of the present invention was found to exhibit high accuracy of CV 0.5%.

In the same manner as above, the diluted blood measured with a round capillary was spot-deposited on an HbA1c slide located below via depressurization through the outlet. This resulted in color development, and the absorbance of the reflected light was measured with a spectrophotometer (MCPD-2000, Otsuka Electronics Co., Ltd.). As a result of the evaluation (N=10), the accuracy of color development was found to be CV 2.2%.

Example 5

A cell-measuring chip having the configuration of the measuring chip 20 according to the second embodiment mentioned herein was evaluated in terms of accuracy.

Blood (1 µl) and a diluent (20 µl) were introduced into an agitation port 22. While an absorption port 23 and an outlet were shielded, those liquids were mixed via agitation with a stirrer. After the liquids were homogenously mixed, the outlet was opened, and the resulting mixture passed through the communication capillary (the first fluid channel 24) with the effect of capillarity, and the liquid was then guided into a plurality of rhombic or oval cellular measuring cells (the second fluid channel 25) orthogonally extended from the fluid channel. Subsequently, the absorption port 23 was opened, the liquid migrated toward a residual liquid-absorbing member 29 (a liquid-absorbing pad), and this member absorbed all the residual liquid other than the liquid that had been introduced and measured in the measuring cell with the effect of capillarity. Thus, the mixed liquid was completely measured and separated. The measured liquid was spread on the HbA1c slide located immediately below. Color development occurred, and the absorbance of the reflected light was measured using a spectrophotometer (MCPD-2000, Otsuka Electronics Co., Ltd.). As a result of the evaluation (N=10), the accuracy of color development was found to be CV 2.0%.

Example 3

A capillary measuring chip having the configuration of the measuring chip according to the third embodiment mentioned herein was evaluated in terms of accuracy.

Blood (1 µl) and a diluent (20 µl) were introduced into an agitation port 42. While an absorption port 43 and an outlet were shielded, those liquids were mixed via agitation with a stirrer. After the liquids were homogenously mixed, the outlet was opened, the resulting mixture passed through the communication capillary (the first fluid channel 44) with the effect of capillarity, and the liquid was then guided into a plurality of measuring capillaries (the second fluid channel 45) orthogonally extended from the fluid channel. Subsequently, the absorption port 43 was opened, the liquid migrated toward a residual liquid-absorbing member 49 (a liquid-absorbing pad), and this member absorbed all the residual liquid other than the liquid that had been introduced and measured in the measuring capillaries with the effect of capillarity of the liquid-absorbing pad. Thus, the mixed liquid was completely measured and separated. The measured liquid was immediately spread on the HbA1c slide at the bottom of the outlet. Color development occurred, and the absorbance of the reflected light was measured using a spectrophotometer (MCPD-2000, Otsuka Electronics Co., Ltd.). As a result of the evaluation (N=10), the accuracy of color development was found to be CV 2.8%.

INDUSTRIAL APPLICABILITY

With the use of the microchip of the present invention, a specimen liquid is directly collected and weighed without using any collecting and weighing devices so as to be immediately supplied to a reaction part. Thus, a specimen liquid can readily be weighed and quantified with high precision. Further, in accordance with the present invention, microweighing in a microchip can be achieved, although it has been difficult to precisely perform microweighing in a microchip by a conventional weighing method.

The invention claimed is:

1. A microchip for analyzing liquid samples, comprising:
   a measuring structure comprising a first fluid channel provided on the chip body;
   a second fluid channel in communication with the first fluid channel at one end of the second fluid channel;
   a third fluid channel in communication with the other end of the second fluid channel;
   and further comprising an agitation port at one end of the first fluid channel of the measuring structure and an absorption port at the other end of the first fluid channel of the measuring structure, wherein:
   the perimeter and the cross-sectional area of the vicinity of an opening of the first fluid channel in communication with the second fluid channel are designated as L1 and S1, respectively, and
   the perimeter and the cross-sectional area of a first opening of the second fluid channel in communication with the first fluid channel are designated as L2 and S2, respectively, and (L1/S1)<(L2/S2).

2. The microchip of claim 1 wherein the perimeter of the first opening of the second fluid channel provided with a level difference is at least a half of the perimeter L2 of the first opening of the second fluid channel.

3. The microchip of claim 1 wherein the perimeter of a second opening of the second fluid channel provided with a level difference is at least a half of the perimeter of the second opening of the second fluid channel.

* * * * *